United States Patent [19]

Baker et al.

[11] Patent Number: 5,686,463
[45] Date of Patent: Nov. 11, 1997

[54] OXADIAZOLES USEFUL IN THE TREATMENT OF SENILE DEMENTIA

[75] Inventors: Raymond Baker, Green Tye; Kevin John Merchant, Bishop's Stortford; Angus Murray MacLeod, Bishops's Stortford; John Saunders, Bishop's Stortford, all of England

[73] Assignee: Merck, Sharp & Dohme, Ltd., Hoddesdon, England

[21] Appl. No.: 27,989

[22] Filed: Mar. 19, 1987

[30] Foreign Application Priority Data

Mar. 27, 1986 [GB] United Kingdom .................. 8607713
Dec. 24, 1986 [GB] United Kingdom .................. 8630896

[51] Int. Cl.⁶ .................. A61K 31/41; A61K 31/435; C07D 413/04; C07D 451/02; C07D 453/02
[52] U.S. Cl. .................. 514/299; 514/304; 514/305; 514/326; 514/340; 546/112; 546/125; 546/133; 546/137; 546/209; 546/269.4; 548/131; 548/133; 548/143
[58] Field of Search .................. 546/133, 137, 546/112, 125, 209, 269.4; 514/305, 299, 304, 326, 340; 548/131, 133, 143

[56] References Cited

U.S. PATENT DOCUMENTS

| | | | |
|---|---|---|---|
| 3,419,575 | 12/1968 | Griss | 548/138 |
| 4,599,344 | 7/1986 | Morgan | 546/137 |
| 4,608,378 | 8/1986 | Falch et al. | 514/302 |
| 4,705,786 | 11/1987 | Yamamoto et al. | 514/252 |
| 4,837,241 | 6/1989 | Jensen et al. | 514/340 |
| 4,933,353 | 6/1990 | Jensen et al. | 514/340 |
| 4,971,975 | 11/1990 | Hadley et al. | 514/299 |
| 4,988,706 | 1/1991 | Hadley et al. | 514/299 |
| 5,043,343 | 8/1991 | Wyman | 514/299 |
| 5,132,316 | 7/1992 | Hadley et al. | 514/361 |

OTHER PUBLICATIONS

*J.Med.Chem.* 29, 1004 (1986), Sauerberg et al.

*Primary Examiner*—Fiona T. Powers
*Attorney, Agent, or Firm*—Robert J. North; Melvin Winokur

[57] ABSTRACT

A class of novel oxadiazoles, substituted on one of the ring carbon atoms with a non-aromatic azacyclic or azabicyclic ring, and substituted on the other ring carbon atom with a substituent of low lipophilicity; are potent muscarinic agonists, and have good CNS penetrability. The compounds are therefore useful in the treatment of neurological and mental illnesses.

24 Claims, No Drawings

OXADIAZOLES USEFUL IN THE TREATMENT OF SENILE DEMENTIA

The present invention relates to a class of oxadiazole compounds which stimulate central muscarinic acetylcholine receptors and therefore may be useful in the treatment of neurological and mental illnesses whose clinical manifestations are due to involvement of specific populations of cholinergic neurones. Such diseases include presenile and senile dementia (also known as Alzheimer's disease and senile dementia of the Alzheimer type respectively), Huntington's chorea, tardive dyskinesia, hyperkinesia, mania and Tourette Syndrome. The compounds of this invention are also useful analgesic agents and therefore useful in the treatment of severe painful conditions such as rheumatism, arthritis, and terminal illness.

Alzheimer's disease, the most common dementing illness, is a slowly progressive neurological disorder characterised by marked deficits in cognitive functions including memory, attention, language and visual perception capabilities. Although abnormalities in several central neurotransmitter systems have been documented (see P. Davies, *Med. Res. Rev.*, 1983, 3, 221–236) in Alzheimer's disease, the most consistent neurochemical deficiency involves presynaptic cholinergic markers in neocortex and hippocampus such as choline acetyl transferase activity, acetylcholinesterase activity and acetylcholine synthesis (see P. J. Whitehouse et al., *CRC Crit. Rev. Clin. Neurobiol.*,1 1985, 1, 319–339). Muscarinic acetylcholine receptor sites located postsynaptically however are generally preserved in patients with Alzheimer's disease.

Directly acting muscarinic agonists capable of stimulating such sites directly should therefore be beneficial in reversing the cholinergic deficiency in Alzheimer's disease and other diseases related to cholinergic dysfunction. However, most muscarinic agonists, including acetylcholine itself, are quaternary ammonium compounds incapable of penetrating the blood-brain barrier to any clinically significant extent following peripheral (e.g. oral) administration. Such agents fail to stimulate the desired central sites but instead induce undesired side-effects mediated exclusively peripherally-located muscarinic acetylcholine receptors.

The compounds of the present invention are potent muscarinic agonists but, being either secondary or tertiary amines with physiochemical properties (lipophilicity and pKa) consistent with CNS penetrability, can stimulate those central sites implicated in the neurodegenerative disorders discussed above.

The present invention provides an oxadiazole, substituted on one of the ring carbon atoms thereof with a non-aromatic azacyclic or azabicyclic ring system; and substituted on the other ring carbon with a substituent of low lipophilicity, or a salt thereof.

The novel compounds of this invention may be represented by structural formula (I):

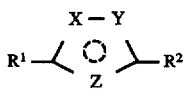

(I)

or a salt thereof; wherein one of X, Y, or Z is an oxygen atom and the other two are nitrogen atoms, and the dotted circle represents aromaticity (two double bonds) thus forming a 1,3,4-oxadiazole or 1,2,4-oxadiazole nucleus; $R^1$ represents a non-aromatic azacyclic or azabicyclic ring system; and $R^2$ represents a substituent of low lipophilicity.

Preferably the oxadiazole ring is a 1,2,4-oxadiazole.

The azacyclic or azabicyclic ring system is a non-aromatic ring system containing one nitrogen atom as the sole hereto atom. Suitably the ring system contains from 4 to 10 ring atoms, preferably from 5 to 8 ring atoms. The bicyclic systems may be fused, spiro, or bridged. Examples of suitable ring systems include the following:

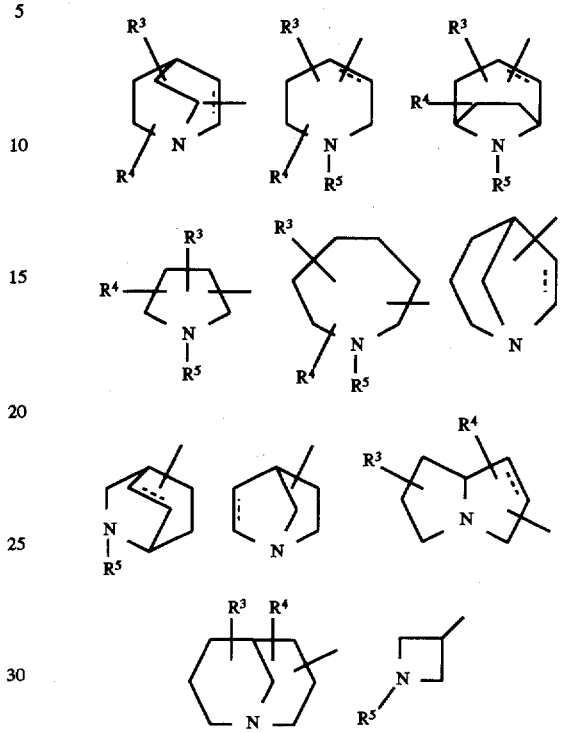

wherein the broken line represents an optional chemical bond:

the substituents $R^3$ and $R^4$ independently represent hydrogen, $C_{1-4}$ alkyl, halo, $C_{1-4}$ alkoxy, hydroxy or carboxy: or $R^3$ and $R^4$ together represent carbonyl;

the group $R^5$ represents hydrogen or $C_{1-4}$ alkyl. It will be appreciated that the nitrogen atom in the azacyclic or azabicyclic ring system will carry a lone pair of electrons.

Suitably the group $R^3$ is hydrogen or methyl; and $R^4$ is hydrogen, methyl or hydroxy. Preferably one or both of $R^3$ and $R^4$ is hydrogen.

Preferably the group $R^5$ represents hydrogen or methyl.

Suitably the azabicyclic ring system is a pyrrolidine, quinuclidine or 1-azabicyclo-[2,2,1]heptane ring. A preferred azabicyclic ring system is quinuclidine, of structure:

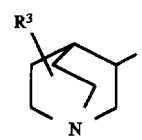

in particular where $R^3$ represents hydrogen, methyl or hydroxy.

The term "low lipophility" is intended to indicate that the group has a Rekker f value (hydrophobic fragment constant: see R. F. Rekker, "The Hydrophobic Fragmental Constant" Elsevier, 1977) of not greater than 1.5. For example the methyl group has a value of 0.7 and the ethyl group a value of 1.26. Indeed we have found that a propyl substituent provides a compound which is an antagonist rather than an agonist.

Thus the substituent of low lipophilcity, represented by the group $R^2$ in formula (I) may be, for example, hydrogen, halogen, —$CF_3$, —$OR^7$, —$N(R^7)_2$, —$NHOR^7$, —$NHNH_2$, —CN, $COR^8$, $C_{2-5}$ alkenyl, $C_{2-5}$ alkynyl, $C_{1-2}$ alkyl, or $C_{1-2}$ alkyl substituted with —$OR^7$, —$N(R^7)_2$, —$SR^7$, —$CO_2R^7$, —$CON(R^7)$ or halogen; wherein $R^7$ is hydrogen or $C_{1-2}$ alkyl, and $R^8$ represents —$OR^7$, $NH_2$, or $NHR^7$.

Preferably the substituent of low lipophilicity is hydrogen, halogen, —$CF_3$, —$OR^7$, —$NHR^7$, —$NHNH_2$, —CN, —CO. $R^8$, $C_{2-3}$ alkenyl, $C_{2-3}$ alkynyl, $C_{1-2}$ alkyl, or $C_{1-2}$ alkyl substituted with —$OR^7$, —$NHR^7$, —$SR^7$, —$CO_2R^7$, —$CON(R^7)_2$ or halogen. Particular values of the substituent, $R^2$, are hydrogen, methyl, amino, methoxycarbonyl, and ethoxycarbonyl. A preferred group $R^2$ is amino.

One sub-class of compounds within the scope of the present invention is represented by formula (II):

$$R^1 - \underset{O}{\underset{|}{\overset{N}{\diagup}}} \hspace{-4pt} \underset{\diagdown N}{\overset{R^2}{\diagup}}$$

wherein $R^1$ and $R^2$ are as defined above; in particular wherein $R^1$ represents pyrrolidine, quinuclidine, tetrahydropyridine, piperidine, dehydrotropane, pyrrolizidine, azabicyclo-octane, any of which groups $R^1$ may be optionally substituted with $C_{1-3}$ alkyl, or hydroxy; and $R^2$ represents $C_{1-2}$ alkyl, amino, or $C_{1-3}$ alkoxycarbonyl.

As used herein, the terms "alkyl" or "alkoxy" wherein the alkyl group is of 3 or more carbons, means straight chain alkyl, branched chain alkyl or cycloalkyl. The terms "alkenyl" and "alkynyl" include straight and branched chain. The term "halo" or "halogen" means fluoro, chloro or bromo-.

Most of the compounds of this invention have at least one asymmetric centre and often more than one; and can therefore exist as both enantiomers and diastereoisomers. In addition some exist as exo and endo isomers. It is to be understood that the invention covers all such isomers and mixtures thereof.

Also included within the scope of the present invention are salts of the novel compounds. It will be appreciated that salts of the compounds for use in medicine will be non-toxic pharmaceutically acceptable salts. Other salts may, however, be useful if the preparation of the compounds of the invention or their non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, and phosphoric acid. Where the novel compound carries a carboxylic acid group the invention also contemplates salts thereof, preferably non toxic pharmaceutically acceptable salts thereof, such as the sodium, potassium, and calcium salts thereof.

The method of treatment of this invention includes a method of treating Alzheimer's disease, senile dementia of the Alzheimer type, Huntington's chorea, tardive dyskinesia, hyperkinesia, mania or Tourette syndrome by the administration to a patient in need of such treatment of an effective amount of one or more of the novel compounds.

This invention therefore also provides a pharmaceutical composition comprising a compound of the invention and a pharmaceutically acceptable carrier.

It is advantageous, in order to reduce unwanted peripherally mediated side-effects, to incorporate into the composition a peripherally acting cholinergic antagonist (or antimuscarinic agent) Thus the compounds of the invention are preferably administered together with a peripheral cholinergic antagonist such as N-methylscopolamine; N-methylatropine propantheline, methantheline, or glycopyrrolate.

The compounds of the invention can be administered orally, parenterally, or rectally at a daily dose of about 0.01 to 10 mg/kg of body weight, preferably about 0.1 to 1 mg/kg and it may be administered on a regimen of 1–4 times a day. When a cholinergic antagonist is administered, it is incorporated at its conventional dose.

The pharmaceutical formulation of this invention preferably are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g., conventional tabletting ingredients such as corn starch, lactose, sucrose, sorbitol, talc, stearic acid, magnesium stearate, dicalcium phosphate, gums and other pharmaceutical diluents. e.g., water, to form a solid preformulation composition containing a homogenous mixture of a compound of the present invention, or a non-toxic pharmaceutically acceptable salt thereof. When referring to these preformulation compositions as homogenous, it is meant that the active ingredient, is dispersed evenly throughout the composition so that the composition may be readily subdivided into equally effective unit dosage forms such as tablets, pills, and capsules. This solid preformulation composition is then subdivided into unit dosage forms of the type described above containing from 0.1 to about 500 mg. of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures or polymeric acids with such materials as shellac, shellac and cetyl alcohol, cellulose acetate, and the like.

The liquid forms in which the novel compositions of the present invention may be incorporated for administration orally or by injection include aqueous solutions, suitably flavoured syrups, flavoured emulsions with edible oils such as cottonseed oil, sesame oil, coconut oil, peanut oil as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinyl-pyrrolidone, and gelatin.

The compounds of this invention may be prepared by a process which comprises reacting a reactive derivative of a carboxylic acid of formula $R^a$—$CO_2H$, with either a compound of formula (IIIA) or (IIIB) or a salt thereof:

$$R^b-\overset{\overset{\displaystyle NOH}{\|}}{C}-NH_2 \quad \text{(IIIA)}$$

$$R^b-\overset{\overset{\displaystyle O}{\|}}{C}-NHNH_2 \quad \text{(IIIB)}$$

wherein one of $R^a$ and $R^b$ is a non-aromatic azacyclic or azabicyclic ring system, and the other is a group of low lipophilicity.

Suitable reactive derivatives of the acid $R^a$—$CO_2H$ include esters, for example $C_{1-4}$ alkyl esters, thio esters, for example pyridylthioester, acid anhydrides, for example $(R^aCO)_2O$, acid halides, for example the acid chloride, orthoesters, and primary, secondary and tertiary amides.

When the compound of formula (IIIA) is employed the product of the reaction is a 1,2,4-oxadiazole. It will be appreciated that the compound (IIIA) can also be considered as the alternative tautomeric form:

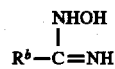

A 3-substituted-1,2,4-oxadiazol-5-yl compound is produced if $R^a$ represents the azacyclic or azabicyclic group and $R^b$ in formula (IIIA) represents the substituent of low lipophilicity. In this case, a preferred reactive derivative of the acid $R^aCO_2H$ is a $C_{1-4}$ alkyl ester. The reaction is conveniently carried out in tetrahydrofuran, dimethylformamide or a lower alkanol such as ethanol, propanol or isopropanol at about 20° to 100° C. for about 1 to 6 hours.

A 5-substituted-1,2,4-oxadiazol-3-yl compound is produced by the process of this invention when $R^a$ represents the substituent of low lipophilicity and $R^b$ represents the azacyclic or azabicyclic group. For this reaction a suitable reactive derivative is the acid chloride or the acid anhydride $(R^aCO)_2O$. The reaction may be carried out by treating compound (IIIA), in the cold, eg from about −5° to +10° C., with the reactive derivative, followed by heating at about 80° C.–120° C. for about 1 to 6 hours.

When the compound of formula (IIIB) is employed, the product of the process of this invention is a 1,3,4-oxadiazole. In this case, a preferred reactive derivative of the acid $R^aCO_2H$ is an orthoester of formula $R^aC(OR^8)_3$ where $R^8$ represents $C_{1-3}$ alkyl. The process is conveniently effected by heating the hydrazide (IIIB) with the orthoester in a solvent such as methanol at reflux temperature for about 2 to 8 hours. An intermediate of formula: $R^bCO.NH.N=C(R^a)OR^8$, may be isolated by evaporation of the solvent. The intermediate is then treated with a strong base such as potassium t-butoxide or 1,8-diazabicyclo[5,4,0]undec-7-ene, in butanol for about 10 to 24 hours at about 90°–150° C.

After the above process is complete, one substituent of low lipophilicity can be converted to another. For example an amino group may be converted to chloro, or hydrazo, —$NHNH_2$, via the intermediacy of diazonium, —$N_2^+$. Similarly, a chloro substituent may be converted by reaction with a nucleophile such as methoxide; and alkoxycarbonyl groups may be converted, via carboxy, to an amino substituent —$NH_2$.

The compounds of this invention may also be prepared by:

a) reacting a compound of formula (IV): $R^a$—CO—N=C($R^b$)N(CH$_3$)$_2$, with hydroxylamine;

b) oxidizing an oxadiazoline with an oxidizing agent such as potassium permanganate, nitrogen dioxide, or N-bromosuccinimide;

c) when the substituent of low lipophilicity is amino, reacting a compound of formula (IIIA) with a cyanogen halide, such as cyanogen bromide.

d) when the substituent of low lipophilicity is ($C_{1-3}$) alkoxycarbonyl, reacting a compound of formula:

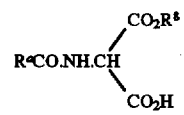

with nitrous acid;

e) when the desired product is a 1,3,4-oxadiazole, reacting a compound of formula $R^a$.CO.NH.NH.CO.$R^b$, with a dehydrating agent, such as $POCl_3$, at an elevated temperature.

The compound of formula (IV) above may be prepared by reacting an amide $R^aCONH_2$, with a compound of formula $(CH_3O)_2C(R^b)N(CH_3)_2$.

In any of the above reactions it may be necessary and/or desirable to protect any sensitive groups in the compounds. For example, if $R^a$ and/or $R^b$ include amino, carboxy, hydroxy or thiol groups, these may be protected in conventional manner. Thus, suitable protecting groups for hydroxy groups include silyl groups such as trimethylsilyl or dimethyl-t.butylsilyl, and etherifying groups such as tetrahydropyranyl; and for amino groups include benzyloxycarbonyl and t.butyloxycarbonyl. Carboxy groups are preferably protected in a reduced form such as in the form of their corresponding protected alcohols, which may be subsequently oxidised to give the desired carboxy group. Thio groups may be protected by disulphide formation, either with the thiol itself or with another thiol to form a mixed disulphide. The protecting groups may be removed at any convenient stage in the synthesis of the desired compound according to conventional techniques.

Certain intermediates employed in the above described processes are novel compounds. Accordingly this invention further provides an oxygenated quinuclidine of formula (V):

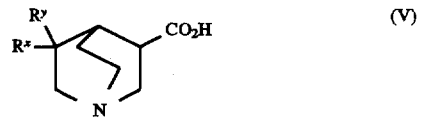

or a reactive derivative thereof wherein $R^x$ represents H and $R^y$ represents hydroxy, or $R^x$ and $R^y$ together represent oxygen. Compound (V) may be prepared by cyclisation of a compound of formula (VI):

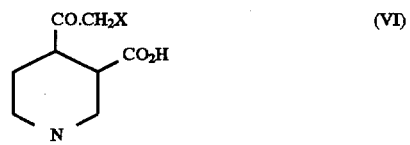

wherein X represents halogen.

The compound (VI) may be prepared by the following synthetic sequence:

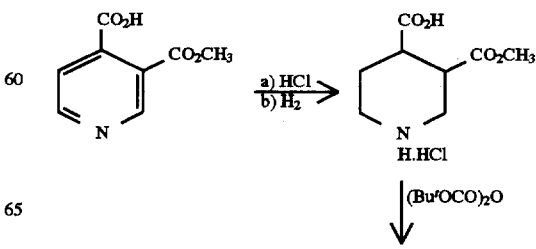

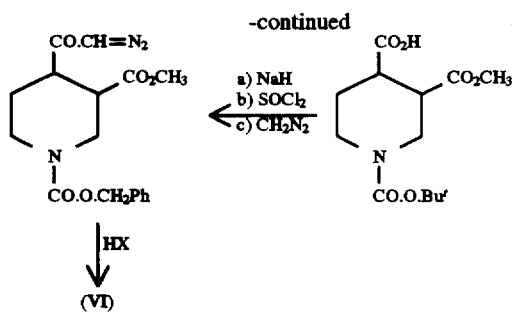

The following Examples illustrate the preparation of compounds according to the invention. Each of the compounds of the Examples demonstrate an affinity for the muscarinic receptor, having an $IC_{50}$ (concentration required to displace 50% of specific [$^3$H]-N-methylscopolamine binding from rat cortical membrane preparations) significantly lower than 100 μm. Agonist behaviour and penetrability into the central nervous system of the compounds of the Examples were assessed in a rat behavioural model by measuring the ability of the compound to elicit a mouth movement response characteristic of centrally-active muscarinic agonists (see Salamone et al, Psychopharm 1986 88,467). In this model, the compounds of all the Examples were active at doses of 10 mg/kg or less.

In the Examples, all temperatures are in °C.; THF is tetrahydrofuran; and ether is diethyl ether.

EXAMPLE 1

1-Methyl-3-[5-(3-methyl-1,2,4-oxadiazol)-yl]pyrrolidine hydrochloride (a) 1-Methyl-3-methoxycarbonyl-2-pyrrolidone To a solution of diisopropylamine (11.3 g, 0.11 mol) in THF (150 ml), at −78° was added n-butyl lithium (60 mls of a 1.6M solution in hexane). The solution was stirred for 0.5 hours before adding N-methyl-2-pyrrolidone (10.1 g; 0.1 mol) in THF (50 ml) over a period of 5 minutes. After 0.75 hours, a solution of dimethylcarbonate (10.8 g: 0.12 mols) in THF (30 ml) was added and the reaction mixture allowed to warm to room temperature overnight. The reaction mixture was poured into water (50 ml) and extracted with dichloromethane (3×150 ml). The combined extracts were dried ($Na_2SO_4$) and evaporated in vacuo. The crude product was chromatographed on silica gel using ethyl acetate/methanol (2:1) as eluant to afford the title product as a clear liquid (4 g). δ($CDCl_3$) 1.90–2.70 (2H, m, $CH_2$); 2.80 (3H, s, $CH_3$) 3.20–3.60 (3H, m, C$\underline{H}$ and C$\underline{H}_2$); 3.70 (3H, s, $CO_2$ $CH_3$).

(b) 1-Methyl-3-methoxycarbonyl-pyrrolidine

This was prepared from the foregoing pyrrolidone by the procedure described by Rapoport (J. Org. Chem., (1974), 39, 893).

(c) 1-Methyl-3-[5-(3-methyl-1,2,4-oxadiazol)-yl]-pyrrolidine hydrochloride

Activated molecular sieves (Type 4A, 1 g) were vigorously stirred in absolute ethanol (25 ml) for 0.5 hours under nitrogen. Sodium metal (0.32 g, 13.9 m.mol) was added and allowed to dissolve before adding acetamide oxime (1.00 g, 13.6 mmol). 1-Methyl-3-carboxymethylpyrrolidine (0.5 g, 3.5 mmols) was added and the reaction mixture heated at 80° for 2 hours. The solution was then decanted from the molecular sieves and the solvent removed in vacuo. Dichloromethane (100 ml) was added to the residue followed by water (20 ml) and the organic products extracted into the dichloromethane layer. The aqueous phase was extracted with dichloromethane (3×50 ml), the combined extracts dried ($Na_2SO_4$), evaporated, and the residue chromatographed through alumina using dichloromethane/methanol (97:3) as eluent, to afford the title oxadiazole as a pale orange liquid (0.2 g).

The product was further purified as the hydrochloride salt, mp. 134° C. (isopropyl alcohol ether); (found. C, 46.46; H, 6.75, N,20.33%. $C_8H_{14}N_3OCl.0.25H_2O$ requires C, 46.15; H, 6.97, N, 20.19%; m/e 167 ($M^+$ of free base); δ(360 MHz, $D_2O$) 2.41 (3H, s, $CH_3$); 2.48 (1H, m, C$\underline{H}$); 2.72 (1H,m,C$\underline{H}$); 3.05 (3H, s, $CH_3$) 3.62–4.20 (5H, m, C$\underline{H}$ and 2×C$\underline{H}_2$).

EXAMPLE 2

1-Methyl-3-[5-(3-ethyl-1,2,4-oxadiazol)-yl]pyrrolidine hydrogen oxalate

This was prepared from 1-methyl-3-methoxycarbonylpyrrolidine and propionamide oxime as described in Example 1. The crude product was purified by chromatography through alumina using dichloromethane/methanol (19:1) as eluent to give the desired oxadiazole as a pale yellow liquid. The product was further purified as the hydrogen oxalate salt mp. 109°, (isopropyl alcohol/ether); (Found: C, 48.86; H, 6.30, N, 15.79%. $C_{11}H_{17}N_3O_5$ requires C, 48.71; H, 6.27, N, 15.50%): m/e 181 ($M^+$ of free base); δ1.22 (3H, t, J=7 Hz, $CH_3$—$CH_2$); 2.24 (1H, m, CH); 2.43 (1H, m, CH); 2.65 (2H, q, J=7 Hz, C$\underline{H}_2$ $CH_3$); 2.75 (3H, s, $CH_3$); 3.21 (2H, m, C$\underline{H}_2$—N); 3.40 (1H, m, C$\underline{H}$—N); 3.59 (1H, m, C$\underline{H}$—N); 3.95 (1H, m, C$\underline{H}$—OX).

EXAMPLE 3

1,3-Dimethyl-3-[5-(3-methyl-1,2,4-oxadiazol)-yl]-pyrrolidine hydrochloride (a) 1,3-Dimethyl-3-methoxycarbonyl-2-pyrrolidone Sodium hydride (0.54 g of an 80% dispersion in oil, 16.5 mmol) was added to a solution of 3-methoxycarbonyl-1-methyl-2-pyrrolidone (2 g, 12 mmols) in THF (50 ml) and the suspension stirred for 0.5 hours. A solution of methyl iodide (3.60 g, 25 mmols) in THF (15 mls) was added and the reaction mixture stirred for 2 hours at room temperature. The solvent was removed in vacuo, and the organic product extracted from the sodium salts with dichloromethane (4×50 mls). The combined extracts were evaporated and the residue chromatographed through silica gel using 3% methanol in ethyl acetate as eluent, to afford the desired amine ester as a pale yellow liquid (1.63 g); δ(60 MHz; $CDCl_3$) 1.45 (3H, s, $CH_3$); 1.55–2.80 (2H, m, C$\underline{H}_2$); 2.88 (3H, s, $CH_3$); 3.10–3.60 (2H, m, $CH_2$); 3.70 (3H, s, $CH_3$).

(b) 1,3-Dimethyl-3-carbomethoxy pyrrolidine

A solution of 1,3-dimethyl-3-methoxycarbonyl-2-pyrrolidine (2.6 g, 15.7 mmol) in THF (50 ml) was added dropwise to a stirred suspension of lithium aluminium hydride (1.79 g, 44.8 mmol) in THF (75 ml) at 0°. The reaction mixture was stirred at 20 for 16 hours and then heated under reflux for 5 hours. Excess reducing agent was destroyed with water and 15% sodium hydroxide and the resultant precipitate filtered. The filtrate was dried ($MgSO_4$) and evaporated to afford crude 1,3-dimethyl-3-hydroxymethylpyrrolidine (1.68 g). This material in water (17.4 ml) and concentrated sulphuric acid (0.74 ml) was treated at 0° with a solution of chromium trioxide (1.09 g), concentrated sulphuric acid (0.74 ml) and water (17.4 ml). The reaction mixture was stirred at 0° for 5 minutes, heated at 100° for 5 minutes and cooled to 0° after which another charge of the chromium trioxide solution was added. Heating at 100° for 0.5 hours was followed by cooling and then sodium metabisulphite was added to destroy excess oxidant.

The pH was adjusted to 10 with 6N-sodium hydroxide, the mixture filtered and the filtrate acidified to pH2 with 6N-HCl. The water was removed in vacuo, and a saturated solution of hydrogen chloride in methanol (200 ml) added to the dry residue. After 16 hours at 20°, the methanol was removed under vacuum, water (75 ml) was added and the pH adjusted to 8 with solid potassium carbonate. The aqueous solution was extracted with dichloromethane (5×50 ml) and the combined extracts dried ($Na_2SO_4$) and evaporated. The residue was chromatographed through alumina using dichloromethane/methanol (49:1) as eluent, to afford the ester as a pale orange liquid (0.82 g); δ(60 MHz, $CDCl_3$); 1.35 (3H, s, $CH_3$); 1.70 (1H, m, C$\underline{H}$); 2.30 (3H, s, $CH_3$); 2.20–3.10 (2H, m, C$\underline{H}_2$) and 3.65 (3H, s, $CH_3$).

(c) 1,3-Dimethyl-3-[5-(3-methyl-1,2,4-oxadiazol)yl] pyrrolidine hydrochloride

This was prepared from the foregoing ester using the method given in Example 1c. The crude product was chromatographed on alumina in ether to give the desired oxadiazole which was further purified by addition of ethereal hydrogen chloride solution to give the hydrochloride salt (0.28 g), m.p. 178° (from isopropanol-ether); (Found: C, 49.59; H, 7.28; N, 19.07. $C_9H_{16}N_3OCl$ requires C, 49.66; H, 7.36, N, 19.31%); m/e 181 ($M^+$ of free base); δ(360 MHz, $D_2O$) 1.67 (3H, s,$CH_3$), 2.39 (3H, s$CH_3$), 2.40 (1H, m, C$\underline{H}$); 2.70 (1H, m,C$\underline{H}$); 3.03 (3H, s, $CH_3$); 3.63 (3H, br m, C$\underline{H}_2$ and C$\underline{H}$) and 4.03 (1H, br s, C$\underline{H}$).

EXAMPLE 4

3-Hydroxy-3-[5-(3-methyl-1,2,4-oxadiazol)-yl]quinuclidine

This was prepared from methyl 3-hydroxyquinuclidine-3-carboxylate (1.85 g, 10 mmol, prepared as described in *Helv. Chim, Acta.*, (1954), 37, 1689) acetamide oxime (4.4 g, 50 mmol) and sodium (1.15 g, 50 mmol) in ethanol (40 ml) in the presence of activated molecular sieves (Type 3A, 10 g) as described in Example 1c. Recrystallization of the crude reaction product from ethyl acetate-petroleum ether (bp 60–80) afforded the desired oxadiazole product (185 mg) m.p. 139°–140°: $R_f$=0.9 on aluminium oxide in 1:9 methanol/dichloromethane; (Found: C, 55.0; H, 7.4; N, 19.1. $C_{10}H_{15}N_3O_2$ requires C, 55.0; H, 7.3; N, 19.2%); m/e 209 ($M^+$); δ($CDCl_3$) 1.32–1.62 (3H, m, 5-$CH_2$ and 8-CH); 2.12–2.22 (2H, m. 4-CH and 8-CH); 2.41 (3H, s, $CH_3$); 2.76–3.01 (5H, m, 2-CH, 6-$CH_2$ and 7-$CH_2$) and 3.71 (1H, A of AB system. J =14 Hz, 2-CH).

EXAMPLE 5

2[5-(3-Methyl-1,2,4-oxadiazol)-yl]-quinuclidine hydrochloride

This was prepared from ethyl quinuclidine-2-carboxylate (1.83 g, 10 mmol) using the same quantities of reagents given in the previous Example 4. The crude free base so obtained was treated in ether with an excess of a saturated ethereal hydrogen chloride. Recrystallization of the resulting salt from isopropanol gave the title compound (0.70 g), m.p. 224, $R_f$ (of free base)=0.6 in methanol-dichloromethane (1:9) on silica; (Found: C, 52.1; H, 6.9; N, 18.3. $C_{10}H_{16}ClN_3O$ requires C, 52.3; H, 7.0; N, 18.3%); m/e 193 ($M^+$ of free base); δ($D_2O$) 1.74–2.0 and 2.03–2.09 (each 2M, each m, 5-$CH_2$ and 8-$CH_2$); 2.31–2.38 (2H, m, 3-$CH_2$); 2.46 (3H, s, $CH_3$); 2.51–2.54 (1H, m, 4-CH); 3.38–3.66 (4H, m, 6-$CH_2$ and 7-$CH_2$) and 5.11–5.17 (1H, m, 2-CH).

EXAMPLE 6

1-Methyl-3-[5-(3-methyl-1,2,4-oxadiazol)-yl]-1,2,5,6-tetrahydropyridine hydrochloride Acetamide oxime (2.54 g, 34 mmol) was added to ethanol (25 ml) which had previously been stirred under dry nitrogen with molecular sieves (10 g, Type 4A) for 1 hour. Sodium (1.15 g, 0.05 mol) was added followed, after 0.5 hours, by methyl 1,2,5,6-tetrahydronicotinate hydrobromide (1 g, 4.2 mmol). The mixture was heated under reflux for 2 hours, cooled, filtered and the filtrate evaporated. The residue in dichloromethane was washed with water and the oil obtained from the organic layer was purified by chromatography on silica in 1:9 methanol-dichloromethane. Treatment of the resulting gum with ethereal hydrogen chloride gave the required oxadiazole hydrochloride (200 mg). m.p. 220°–222°; (Found: C, 49.9; H, 6.4; N, 19.2. $C_9H_{13}N_3O.HCl$ requires C, 50.1; H, 6.5; N, 19.5% ); m/e 179 ($M^+$ of free base); δ($CD_3OD$) 1.57 (3H, s, $CH_3$); 1.96–2.05 (2H, m, 5-$CH_2$); 2.26 (3H, s, $NCH_3$); 2.70 (2H, broad t, J =6 Hz, 6-$CH_2$); 3.42 (2H, broad s, 2-$CH_2$) and 6.42–6.47 (1H, m, 4-CH).

EXAMPLE 7

1-Methyl-3-[5-(3-ethyl -1,2,4-oxadiazol)-yl]-1,2,5,6-tetrahydropyridine hydrochloride This was prepared starting from methyl 1,2,5,6-tetrahydronicotinate hydrobromide (1 g, 4.2 mmol), propionamide oxime (3.7 g, 42 mmol) and sodium (0.92 g, 40 mmol) as described in Example 6. The material was isolated as its hydrochloride salt (600 mg), m.p. 160°–162°; (Found: C, 51.4; H, 7.2; N, 17.6. $C_{10}H_{15}N_3O.HCl.0.25 H_2O$ requires C, 51.3; H, 7.1; N, 17.9%); m/e 192 ($M^+$–1 for free base); δ($D_2O$) 1.31 (3H, t, J =7 Hz, $CH_2$C$\underline{H}_3$); 2.81 (2H, q. J =7 Hz, C$\underline{H}_2CH_3$); 2.83–2.86 (2H, m, 5-$CH_2$); 3.11 (3H, s, $NCH_3$); 3.6 (2H, broad s, 6-$CH_2$); 4.20 (2H, broad s, 2-$CH_2$) and 7.34 (1H, m, 4-CH).

EXAMPLE 8

1-Methyl-3-[5-(3-methyl-1,2,4-oxadiazol)-yl]piperidine hydrochloride

This was prepared as described in Example 6 but substituting ethyl 1-methylpiperidine -3-carboxylate (1.0 g) to give the title compound (700 mg); m.p. 245°–246° (from isopropanol-ether): (Found: C, 49.6; H, 7.4; N, 19.4. $C_9H_{15}N_3O.HCl$ requires C, 49.7; H, 7.4; N, 19.3%); m/e 181 ($M^+$–1 for free base); δ($CDCl_3$) 1.57–1.70 (2H, m, $CH_2$); 2.02–2.06 (2H, m, $CH_2$); 2.38 (3H, s, $CH_3$); 2.43–2.58 and 2.60–3.01 (2H, each m, 6-$CH_2$); 2.89 (3H, broad s, $NCH_3$); 3.58–3.62 and 3.83–3.88 (each 1H, each broad d, J =10 Hz, 2-$CH_2$) and 4.02–4.11 (1H, m, 3-CH).

EXAMPLE 9

1-Methyl-4-[5-(3-methyl-1,2,4-oxadiazol)-yl]piperidine hydrochloride

This was prepared from ethyl 1-methyl-piperidine-4-carboxylate (1 g, 5.8 mmol), acetamide oxime (1.68 g. 22.7 mmol) and sodium (0.7 g, 30 mmol) following the directions given in Example 6. After treatment of the intermediate free base with ethereal hydrogen chloride purification of the salt by recrystallization from isopropanol-ether gave the desired oxadiazole hydrochloride (600 mg): m.p. 175°–176°; (Found: C, 48.6; H, 7.5; N, 18.9. $C_9H_{15}N_3O.HCl. 0.25H_2O$ requires C. 48.6; H, 7.5; N, 18.9%); m/e 181 ($M^+$–1 for free base); δ($CDCl_3$) 2.07(2H,q, J =11 Hz, 3- and 5-axial CH); 2.39 (3H, s, $CH_3$); 2.41–2.49 (2H, m, 3- and 5-equatorial CH); 2.94 (3H, s, $NCH_3$); 3.20 (2H, overlapping dd, J =11 Hz, 2-and 6-axial CH); 3.39–3.52 (1H, m, 4-CH) and 3.69 (2H, d, J =11 Hz; 2-and 6-equatorial CH).

EXAMPLE 10

3-[3-(5-Methyl-1,2,4-oxadiazol)-yl]quinuclidine hydrochloride (a) Quinuclidinone (24.2 g, 0.19 mol) and 2,4,6-triisopropylbenzene sulphonohydrazide (72 g, 0.24 mol) (250 ml) were stirred together in anhydrous methanol for 3 hours. Potassium cyanide (33.8 g, 0.51 mol) was added and the mixture heated under reflux for 5 hours. The material isolated, after evaporation of the solvent, was partitioned between water and dichloromethane. The organic phase was dried (sodium sulphate) and evaporated and the residue fractionally distilled under reduced pressure to give 3-cyano-quinuclidine (6.1 g), approximate b.p. 95°–100° at 13 N.m$^{-2}$ (0.1 mmHg).

(b) A portion of the foregoing nitrile (1.36 g, 10 mmol) was treated in refluxing ethanol (40 ml) for 16 hours with hydroxylamine hydrochloride (2.08 g, 30 mmol) and potassium carbonate (2.8 g, 20 mmol). The residue obtained after evaporation of the ethanol was dried over phosphorous pentoxide and then treated at 0° with acetic anhydride (40 ml). The mixture was heated under reflux for 3 hours, excess acetic anhydride removed and the residue partitioned between dichloromethane and saturated potassium carbonate solution. The material isolated from the organic phase was purified by chromatography on neutral alumina (Grade III) in 1% methanol in dichloromethane. Treatment of the resulting oil with ethereal hydrogen chloride followed by recrystallization of the salt from isopropanol-ether gave the required oxadiazole hydrochloride (610 mg); m.p. 191° (dec); (Found: C, 51.6; H, 6.9; N, 18.0. $C_{10}H_{15}N_3O.HCl$ 0.25$H_2O$ requires C, 51.3; H, 7.1; N, 17.9%); m/e 193 (M$^+$ of free base); δ($D_2O$) 1.85–1.91 and 2.15–2.19 (each 2H, each m, 5-and 8-$CH_2$); 2.54 (1H, dd, J=4.5 Hz, 4-CH); 2.63 (3H, s, $CH_3$); 3.3–3.47 (4H, m, 6-and 7-$CH_2$); 3.6–3.71 (1H, m, 3-CH) and 3.76–3.82 (2H, m, 2-$CH_2$).

EXAMPLE 11

3-[5-(3-Methyl-1,2,4-oxadiazol)-yl]quinuclidine hydrochloride

Using the procedure outlined in Example 1c, methyl 3-quinuclidine carboxylate (0.67 g, 3.9 mmol; prepared as described by Grob in Helv. Chim. Acta., (1954), 37, 1689), acetamide oxime (1.78 g, 24.1 mmol) and sodium (0.09 g, 3.9 mmol) gave, after heating under reflux in ethanol for 4 hours, the required oxadiazole. Treatment of this material in ether with hydrogen chloride in ether followed by recrystallization of the resulting solid from dichloromethane-ether, gave the hydrochloride salt (0.43 g), m.p. 185°–187°; (Found: C, 50.34; H, 7.00; N, 17.66. $C_{10}N_{15}H_3O.HCP$ 0.5$H_2O$ requires C, 50.31; H, 7.18; N, 17.60%); m/e 193 (M$^+$ of free base); δ(CDCl$_3$) 1.81–1.93 and 2.07–2.27 (each 2H, each m, 5-$CH_2$ and 8-$CH_2$); 2.41 (3H, s, $CH_3$); 2.58–2.62 (1H, m, 4-CH); 3.34–3.48 and 3.50–3.61 (4H, each m, 6-$CH_2$ and 7-$Ch_2$) and 3.69–3.76 and 3.86–3.92 (1H and 2H, each m, 2-$CH_2$ and 3-CH).

EXAMPLE 12

3-[5-(3-Methyl-1,2,4-oxadiazol)-yl]-2,3-dehydroquinuclidine hydrochloride

This was prepared as described in Example 1c but starting from methyl 2,3-dehydroquinuclidine-3-carboxylate (0.5 g, 2.99 mmol), sodium (0.07 g, 7.99 mmol) and acetamide oxime (1.33 g, 17.96 mmol). The product isolated after chromatography on alumina eluting first with ethyl acetate and then 4% methanol in ethyl acetate was recrystallized from dichloromethane-hexane to give 2-(1-aminoethylidenaminoxy)-3-[5-(3-methyl-1,2,4-oxadiazol)-yl]quinuclidine (0.15 g). This material (0.25 g, 0.94 mmol) in dichloromethane (30 ml) was treated for 15 minutes at 20 with potassium t-butoxide (1 g). After filtration, the material isolated from the filtrate was purified by alumina chromatography in methanol-dichloromethane (1:49). The solid obtained after addition of ethereal hydrogen chloride was recrystallized from ether-dichloromethane to give the desired oxadiaxole (0.11 g): m.p. 167.5°–169°; (Found: C, 52.59; H, 6.17; N, 18.45. $C_{10}H_{13}N_3O.HCl$ requires C, 52.75; H, 6.2; N, 18.46): m/e 191 (M$^+$ for free base); δ($D_2O$) 1.85–1.94 and 2.18–2.26 (each 2H, each m, 5-$CH_2$ and 8-$CH_2$); 2.46 (3H, s, $CH_3$); 3.23–3.32 and 3.70–3.78 (2H, and 3H, each m, 6-$CH_2$, 7-$CH_2$ and 4-CH) and 7.69 (1H, d, J=1.4 Hz, 2-CH).

EXAMPLE 13

2-Methyl-3-[5-(3-methyl-1,2,4-oxadiazol)-yl]quinuclidine hydrochloride (a) 2-Methyl-3-methoxycarbonyl-2,3-dehydroquinuclidine 2-Methyl-3-oxoquinuclidine was prepared by the method of Nielsen (J.Org. Chem., (1966), 31, 1053) and converted to its hydrochloride salt by treatment with ethereal hydrogen chloride.

The salt prepared above (17.5 g, 0.1 mol) was dissolved in water (17 ml) and cooled to 0°. Sodium cyanide (4.0 g, 0.1 mol) in water (15 ml) was added dropwise and the reaction was stirred at 5 for 16 hours then filtered to give a white solid which was heated under reflux for 16 hours in concentrated hydrochloric acid (100 ml). The reaction was cooled then concentrated in vacuo to give a solid which was treated (for 50 hours at room temperature) with methanol saturated with hydrogen chloride. The solution was concentrated in vacuo and the residue heated under reflux in thionyl chloride (55 ml) for 16 hours then cooled and concentrated under reduced pressure. The residue was dissolved in water which was made basic with potassium carbonate and extracted with dichloromethane. The organic phase was dried with sodium sulphate and concentrated to give an oil which was chromatographed on neutral alumina (grade 3) eluting with dichloromethane, thus yielding 2-methyl-3-methoxycarbonyl-2,3-dehydroquinuclidine (2.6 g) which was characterised as its hydrogen chloride salt m.p. 198°–199°; Rf=0.33 in dichloromethane on alumina; (Found C, 54.9; H, 7.3; N, 6.6; Cl, 16.8. $C_{10}H_{16}ClNO_2$ requires C, 55.2; H, 7.6, N, 6.4; Cl, 16.3%): m/e 181 (M$^+$ for free base): δ(CDCl$_3$) 1.73–1.84 and 1.98–2.08 (each 2H. each m, 5-$CH_2$ and 8-$CH_2$); 2.41 (3H, s, $CH_3$); 3.18–3.27 and 3.53–3.60 (each 2H, each m, 6-$CH_2$ and 7-$CH_2$), 3.49–3.53 (1H, m, 4-CH) and 3.84 (3H, s, $OCH_3$).

(b) The ester (650 mg, 3.6 mmol) prepared as described above was treated with hydrogen gas at 2.8×10$^5$ N.m$^{-2}$ (40 psi) over 10% Pd—C in ethanol (40 ml) until uptake of gas ceased. The reaction mixture was filtered and concentrated in vacuo to give a colorless oil which was then added to a mixture containing molecular sieves (Type 4A) (10 g), sodium ethoxide solution from sodium (466 mg, 20 mmol) and ethanol (30 ml), and acetamide oxime (1.6 g, 21.6 mmol). The mixture was heated under reflux for 90 minutes then cooled, filtered and concentrated in vacuo. The residue was dissolved in water and extracted with ether which was dried with sodium sulphate. To this ether solution was added ethereal hydrogen chloride. The precipitated white solid was recrystallized from dichloromethane-ether yielding the quinuclidine oxadiazole (390 mg) hydrogen chloride salt m.p. 222° C.; Rf 0.67 in $CH_2Cl_2$ containing 3% methanol on alumina: m/e 207 (M⁺): (Found C, 54.3; H, 6.6; N17.2; Cl, 15.4. C₁₁H₁₆ClN₃O requires C, 54.6; H, 6.7; N, 17.4; Cl,14.7%): δ(CDCl₃) 1.57 (3H, d, J=6 Hz, CHCH₃): 1.88–1.95 and 2.02–2.22 (each 2H, each m, 5-CH₂ and 8-CH₂); 2.40 (3H, s, CH₃), 2.60–2.66 (1H, m, 4-CH), 3.30–3.63 (5H, m, 3-CH, 6-CH₂ and 7-CH₂) and 4.01–4.10 (1H, m, 2-CH).

EXAMPLE 14

2-[5-(3-Methyl-1,2,4-oxadiazol)-yl]-2,3-dehyrotropane hydrochloride

Methyl 3-oxopropane-2-carboxylate 19.7 g, 49 mmol; prepared as described in *J. Org. Chem.*, (1957), 22, 1385 in methanol (150 ml) was treated at 0° with sodium borohydride (3.7 g, 98 mmol) added portionwise over 0.5 hours. After 1 hour at room temperature, water (400 ml) was added and the mixture extracted with dichloromethane. The material isolated from the combined organic extracts was purified by chromatography on alumina (Grade III) in 3% methanol in dichloromethane to afford the hydroxyester (1.5 g), R𝒇=0.53 on alumina in 1:9 methanol dichloromethane. A portion of this material (730 mg. 3.6 mmol) was treated at 5° with thionyl chloride (15 ml) and the solution heated under reflux for 2.25 hours. Excess thionyl chloride was removed and the residue in dichloromethane was treated with an excess of cold saturated potassium carbonate solution. The organic layer was evaporated and the resulting oil was combined with the product from a similar preparation and used directly in the next step. Using the procedure given in Example 1c, the foregoing unsaturated ester (770 mg, 4.2 mmol), sodium (0.48 g, 21 mmol) and acetamide oxime (1.55 g, 21 mmol) gave the required oxadiazole after a reaction of time of 0.5 hours. Upon cooling, acetic acid (1.26 g, 21 mmol) was added before removing the molecular sieves by filtration. The filtrate was evaporated and the residue partitioned between dichloromethane and water made basic by addition of solid potassium carbonate. The material isolated from the organic solvent was purified by chromatography on alumina in ethyl acetate and the resulting yellow oil in ether treated with ethereal hydrogen chloride. Recrystallization of the salt from isopropanol gave the oxadiazole hydrochloride (135 mg). m.p. 201°–202° ; R𝒇=0.84 on alumina in 10% methanol in dichloromethane; (Found: C, 54.3; H, 6.6; N, 17.0. C₁₁H₁₅N₃O.HCl requires C, 54.7; H, 6.7; N, 17.4%); m/e 205 (M⁺ of free base); δ(D₂O) 2.05–2.11 and 2.39–2.72 (4-H, each m, 6-CH, and 7-CH₂); 2.43 (3H, s, CH₃); 2.94 (3H, s, NCH₃); 3.02–3.21 and 4.12–4.16 (each 1H, each m, 4-CH₂); 4.70–4.86 (2H, m, 1-CH and 5-CH) and 7.09–7.25 (1H, m, 3-CH).

EXAMPLE 15

3-[2-(5-Methyl-1,3,4-oxadiazol)-yl]quinuclidine hydrogen oxalate (a) Quinuclidine-3-carboxyhydrazide Methyl quinuclidine-3-carboxylate hydrochloride (10 g, 4.87 mmol) was partitioned between dichloromethane and 2M-potassium carbonate solution. The material isolated from the organic layer was dissolved in methanol (10 ml) and hydrazine hydrate (2 ml) and the solution heated under reflux for 22 hours. Evaporation of the solvents in vacuo yielded the hydrazide (0.85 g) which was characterised as its dihydrochloride salt, m.p. 227°–230°; R𝒇=0.3 on alumina in methanol-dichloromethane (1:9): (Found: C, 39.4; H, 7.2; N, 16.9; C₁.₂₈.₄ C₈H₁₅N₃O. 2HCl.0.2H₂O requires C, 39.1; H, 7.1; N, 17.1; Cl, 28.8%); Vₘₐₓ (Nujol) 3300–2500, 2040, 1980 and 1700 cm⁻¹; m/e (free base) 169 (M⁺); δ(D₂O) 1.85–1.93 (2H, m, 5-CH₂); 2.00–2.09 (2H, m, 8-CH₂): 2.41–2.46 (1H, m, 4-CH): 3.19–3.21 (1H, m, 3-CH); 3.30–3.37 (4-H, m, 6-CH₂, and 7-CH₂); 3.44 (1H, ddd, J=13 Hz, 13 Hz and 2 Hz, 2-CH anti to CO) and 3.72 (1H, ddd, J=13 Hz, 5.5 Hz and 1.5 Hz, 2-CH syn to CO).

(b) 3-[2-(5-Methyl-1,3,4-oxadiazol)-yl]quinuclidine hydrogen oxalate

A solution of the foregoing hydrazide (0.862 g, 5.1 mmol) in methanol (20 ml) and trimethyl orthoacetate (6.5 ml, 51 mmol) was heated under reflux for 4 hours, cooled, and the solvent evaporated in vacuo. The residue was dissolved in 1-butanol (20 ml), potassium t-butoxide (0.86 g, 7.7 mmol) added and the solution heated under reflux for 17 hours. After removal of the solvent in vacuo, the residue was partitioned between dichloromethane and 2M potassium carbonate solution. The material isolated from the organic layer was purified by chromatography on grade 3 alumina in 1% methanol in dichloromethane to yield the desired oxadiazole (170 mg), which was characterised as its oxalate salt: m.p. 97°–105°; R𝒇=0.2 on alumina in 2% methanol in dichloromethane; (Found: C, 46.9; H, 5.6; N, 12.7. C₁₀H₁₅N₃O.1.6(HO₂C)₂ requires C, 47.0; H, 5.4; N, 12.5%); m/e 193 (M⁺ of free base); δ(D₂O) 1.81–1.98 (2H, m, 8-CH₂): 2.11–2.18 (2H, m, 5-CH₂); 2.54 (3H, s, CH₃); 2.58–2.61 (1H, m, 4-CH); 3.31–3.45 (4H, m, 6-CH₂, and 7-CH₂) and 3.75–3.83 (3H, m, 2-CH₂ and 3-CH).

EXAMPLE 16

3-[5-(3-Amino-1,2,4-oxadiazol)-yl]quinuclidine

Sodium metal (1.56 g, 0.068 mol) was added to a suspension of molecular sieve (type 4A, 12 g) in absolute ethanol (60 ml) stirred under nitrogen. After 15 minutes at room temperature, hydroxyguanidine hemisulphate hemihydrate (4.72 g, 0.035 mol) was added and stirring continued a further 1 hour. Methyl quinuclidine-3-carboxylate (1 g, 0.0059 mol) was added to the mixture which was then heated under reflux for 2 hours. After removal of the molecular sieve by filtration, the filtrate was evaporated in vacuo and the resulting gum partitioned between dichloromethane and water. The material isolated from the organic layer was recrystallised from isopropanol-petroleum ether (b.p. 40–60) to afford the required amino-oxadiazole (490 mg), m.p. 158°–160°; (Found: C, 55.5; H, 7.4; N, 28.5. C₉H₁₄N₄O requires C, 55.7; H, 7.4; N, 28.9%); m/e 194 (M⁺); δ(CDCl₃) 1.36–1.48 (1H, m, 8-CH): 2.60–2.73 (3H, m, 8-CH and 5-CH₂); 2.17–2.23 (1H, m, 4-CH); 2.79–3.08 (5H, m, 6-CH₂ 7-CH₂ and 2-CH); 3.21–3.38 (2H, m, 3-CH and 2-CH) and 4.43 (2H, broad s, NH₂).

EXAMPLE 17A endo-2-[5-(3-Amino-1,2,4-oxadiazol)-yl]pyrrolizidine (a) 2-Methoxycarbonyl-3H-pyrrolizine This was prepared from pyrrole-2-aldehyde by the procedure described by Flitsch et al (Chem. Ber., (1968), 101, 3843).

(b) endo-2-Methoxycarbonylpyrrolizidine

This was prepared from 2-methoxycarbonyl-3H-pyrrolizine as described by Brandange et al, (Acta. Chem. Scand., (1973), 27, 433.

(c) endo-2-[5-(3-Amino-1,2,4-oxadiazol)-yl]pyrrolizidine

Activated molecular sieves (Type 4A, 0.5g) were vigorously stirred in absolute ethanol (25 ml) for 0.5 hr under nitrogen. Hydroxy guanidine sulphate (2.4 g, 9.0 mmol) was added and the reaction mixture stirred at room temperature for 1 hr. Sodium metal (0.76 g; 33 mmol) was added and allowed to dissolve before adding a solution of endo-2- methoxycarbonylpyrrolizidine (0.56 g; 3.3 mmol) in ethanol (2 ml). After heating the reaction at reflux temperature for 2 hr. the solution was decanted from the molecular sieves and the solvent removed in vacuo. Dichloromethane (150 ml) was added to the residue followed by water (15 ml) and the material isolated from the organic layer was dried ($Na_2SO_4$) and evaporated, and the residue chromatographed through alumina using dichloromethane/MeOH (95:5) as eluant to afford the title amino oxadiazole as a white crystalline solid (0.37 g) mp. 133°–135° C. (isopropyl alcohol/petroleum ether): (Found: C, 54.99; H, 7.22; N, 27.96 $C_9H_{14}N_4O.0.25 H_2O$ requires C, 54.40;H, 7.30; N, 28.21%: m/e 194 ($M^+$); δ(360 MHz, $CDCl_3$) 1.20–2.10 (6H, m, 3× $CH_2$): 2.25–3.00 (2H, m, $CH_2$—N): 3.10 (1H, dd, J=11, 7.2 Hz, CH—N): 3.24 (1H, dd, J=11, 7.2 Hz, CH—N); 3.38–3.72 (2H, m, 2×CH); and 4.32 (2H, br s, $NH_2$).

EXAMPLE 17B exo-2-[5-(3-Amino-1,2,4-oxadiazol)-yl]pyrrolizidine

Activated molecular sieves (Type 4A, 0.5 g) were vigorously stirred in absolute ethanol (25 ml) for 0.5 hr under nitrogen. Hydroxy guanidine sulphate (2.4 g, 9.0 mmol) was added and the reaction mixture stirred at room temperature for 1 hr. Sodium metal (0.76 g; 33 mmol) was added and allowed to dissolve before adding a solution of endo-2-methoxycarbonylpyrrolizidine (0.56 g; 3.3 mmol) in ethanol (3 ml). After 48 hr at reflux temperature, the solution was decanted from the molecular sieves and the solvent removed in vacuo. Dichloromethane (150 ml) was added to the residue followed by water (15 ml) and the organic products isolated from the dichloromethane layer were chromatographed on alumina using dichloromethane/MeOH (95:5) as eluent to afford a 1:1 mixture of endo-and exo-oxadiazoles (0.15 g). Further chromatography of the mixture through silica-gel using dichloromethane/MeOH (60:40) as eluent gave a fraction enriched 3:1 in the exo-isomer, as a white crystalline solid, mp. 94°–99° (isopropylalcohol/petroleum ether); (Found: C, 54.07; H, 7.23; N, 27.84 $C_9H_{14}N_4O.0.25H_2O$ requires C, 54.40; H, 7.30; N, 28.21); m/e 194 ($M^+$); δ(360 MHz, $CDCl_3$) 1.50–2.10 (6H, m, 3×$CH_2$): 2.25–2.60 (2H, m, $CH_2$—N); 3.00–3.25 (2H, m, $CH_2$—N): 3.38–3.60 (2H, m, 2×C—H): 4.32 (2H, br s, $NH_2$).

EXAMPLE 18 endo and exo-1-[5-(3-Amino-1,2,4-oxadiazol)-yl] pyrrolizidines (a) 1-Methoxycarbonylpyrrolizid-1-ene This was prepared from 1-pyrroline-1-oxide and methyl γ-hydroxycrotonate as described by Tufariello et al, (J. Org. Chem., (1975), 40, 3866).

(b) endo-1-Methoxycarbonylpyrrolizidine

A solution of 1-methoxycarbonylpyrrolizid-1-ene (0.75 g, 4.5 mmol) in acetic acid (75 mls) was subjected to hydrogenation over rhodium on alumina (0.3 g) in a parr shaker. After 1 hr the solvent was removed under vacuum, water (20 ml) added and the solution made basic with potassium carbonate. The aqueous phase was extracted with chloroform (4×75 mls), the combined extracts dried ($Na_2SO_4$) and evaporated to afford the title endo-ester (0.65 g). The product was further purified as the hydrochloride salt, mp 129°–131° (isopropylalcohol/ether): (Found: C, 50.68; H, 7.83; N, 6.62. $C_9H_{15}NO_2$ 0.5$H_2O$ requires C, 50.35; H, 7.93; N, 6.53%); δ(60 MHz; $D_2O$) 1.60–3.40 (11H, m, 5×$CH_2$ and 1×CH): 3.70 (3H, s, $CO_2$me) and 3.87–3.94 (1H, m, C H—N).

(c) endo and exo-1-[5-(3-Amino-1,2,4-oxadiazol)-yl] pyrrolizidine

Activated molecular sieves (Type 4A, 0.5 g) and hydroxy guanidine sulphate (1.26 g, 4.73 mmol) were vigorously stirred in THF (60 ml) for 0.25 hr, under nitrogen. Sodium hydride (0.56 g of an 80% dispersion in oil; 24 mls) was added and the reaction mixture heated at 80° C. for 0.5 hr before adding a solution of endo-1-methoxy-carbonyl-pyrrolizidine (0.8 g, 4.73 mmol) in THF (10 ml). After heating at reflux temperature for 4 hr, the reaction mixture was allowed to cool, poured into water (10 ml) and extracted with dichloromethane (3×75 ml). The combined extracts were dried ($Na_2SO_4$), evaporated, and the residue chromatographed on alumina using dichloromethane/MeOH (93.7) as eluent to afford the title amino-oxadiazoles as a 1:1 mixture (0.25 g). Further chromatography of the mixture through silica-gel using dichloromethane/MeOH (60:40) as eluent gave the endo and exo-oxadiazoles as two separated components. The less polar product, assigned exo, was isolated as a white crystalline solid, mp 155°–156° (isopropylalcohol); (Found: C, 55.37; H, 7.32; N, 29.21 $C_9H_{14}N_4O$ requires C, 55.67; H, 7.22; N, 28.87%): δ(360 MHz, $CDCl_3$) 1.63–2.40 (6H, m, 3×$CH_2$); 2.58–2.78 (2H, m, $CH_2$—N): 3.05–3.12 (2H, m, $CH_2$—N): 3.30–3.40 (1H, m, CH-oxadiazole); 3.65–3.75 (1H, m, CH—N) and 4.20 (2H, br s, $NH_2$).

The more polar product, assigned endo was isolated as a white crystalline solid, mp. 137°–140°, (isopropylalcohol): (Found: C, 55.12; H, 7.38, N, 29.25 $C_9H_{14}N_4O$ requires C, 55.67; H, 7.22; N, 28.87%): δ(360 MHz, $CDCl_3$) 1.20–1.25 (1H, m, 0.5×$CH_2$); 1.70–1.77 (3H, m, 1.5×$CH_2$); 2.11–2.38 (2H, m, $CH_2$) 2.50–2.60 (1H, m, 0.5×$CH_2$—N); 2.85–2.95 (1H, m, 0.5×$CH_2$—N). 3.05–3.15 (2H, m, $CH_2$—N); 3.50–3.60 (1H, m, CH-oxadiazole); 3.81–3.89 (1H, m, C H—N) and 4.20 (2H, br s, $NH_2$).

EXAMPLE 19 endo and exo-6-[5-(3-Amino-1,2,4-oxadiazol)-yl]-1-azabicyclo[3.2.1]octane (a) 1-carboethoxymethyl-3-carboethoxypiperidine Ethyl bromoacetate (21.2 g, 127 mmol) was added dropwise to a solution of 3-carboethoxypiperidine (40 g, 254 mmol) in ether 250 ml, at 0° C. The reaction mixture was refluxed for 1 hr, the resultant precipitate filtered off and washed several times with ether. The combined filtrates were evaporated to afford the title piperidine ester (27.6 g); δ(60 MHz, $CDCl_3$) 1.25 (3H, t, J=7 Hz, O—$CH_2$—$CH_3$); 1.27 (3H, t, J=7$H_2$, O—$CH_2$-Me); 1.40–3.70 (9H, m, 4×$CH_2$ and CH—$CO_2$ Et); 3.20 (2H, s, $CH_2$—$CO_2$ Et); 4.10 (2H, q, J=7 Hz, $CH_2$-Me) and 4.15 (2H, q, J=7$H_2$, $CH_2$-Me).

(b) 1-Azabicyclo[3.2.1]octan-6-one

A mixture of ethanol (9 ml) and toluene (10 ml) was added dropwise to a rapidly stirred suspension of potassium (6 g) in toluene (30 ml). at 120° C. After all the ethanol had been added the reaction mixture was stirred at 120° C. for 1 hr before adding a solution of 1-carboethoxymethyl-3-carboethoxy piperidine (15 g, 61.7 mmol) in toluene (40 ml) dropwise at 140° C. The reaction mixture was heated for 3 hr at 140° C. before adding concentrated hydrochloric acid (3×50 ml), and refluxing the aqueous phase for 16 hr. The solvent was removed in vacuo, water (100 ml) added and the solution neutralised with potassium carbonate. The solution was extracted with dichloromethane (3×150 ml, the combined extracts washed with saturated sodium chloride solution, dried ($Na_2SO_4$) and evaporated. The crude product was chromatographed through slicia-gel, eluting with dichloromethane/methanol (90:10) to give 1-azabicyclo [3:2:1]octan-6-one as a crystalline solid (1.1 g): mp. 83°–87° (hexane): m/e 125 ($M^+$): δ(360 MHz, $CDCl_3$) 1.30–2.40

(5H, m, 2×CH$_2$, and CH): 3.12 (2H, s, C$\underline{H}_2$—N); 2.60–3.60 (4H, m, 2×C$\underline{H}_2$—N).

(c) 6-(-1,3-Dithian-2-ylidene)-1-azabicyclo[3.2.1]octane n-Butyl lithium (6.05 ml of a 1.6M solution in hexane, 9.7 mmol) was added dropwise to a solution of 2-trimethylsilyl-1,3-dithiane (1.86 g, 9.7 mmol), in THF (30 ml) at -30° C. and the reaction mixture stirred for 2 hr. A solution of 1-azabicyclo [3.2.1]octan-6-one (1.1 g, 8.8 mmol) in THF (10 ml) was added dropwise and the reaction mixture allowed to warm to room temperature. Water (20 ml) was added and extracted (3×50 ml) with dichloromethane. The combined extracts were dried (MgSO$_4$) and evaporated and the residue chromatographed through alumina eluting with dichloromethane/methanol (97:3) to afford the title compound as a clear liquid, (2 g), m/e 227 (M$^+$); δ(60 MHz; CDCl$_3$) 1.10–2.90 (15H, m, 7×CH$_2$ and CH); 3.38 (2H, AB q, J=17 Hz, C$\underline{H}_2$—C═C).

(d) 6-Carbomethoxy-1-azabicycl[3.2.1]octane

The preceding dithiovinylidene (2 g; 8.8 mmol) was dissolved in methanol, saturated with hydrogenchloride, (75 ml) and stirred at 55° C. for 5 hr. The solvent was removed in vacuo, the residue taken up into water (7 ml), basified to pH 10 with potassium carbonate and extracted into dichloromethane (4×50 mls). The combined extracts were dried (Na$_2$SO$_4$), evaporated, and the residue chromatographed through alumina using dichloromethane/methanol (96.4) as eluent to afford the desired ester as a clear liquid (0.5 g). The hydrochloride salt was prepared, mp 151°–154° (isopropyl alcohol); (Found: C, 51.92; H, 7.65; N, 6.83. C$_9$H$_{16}$NO$_2$Cl 0.125H$_2$O requires C, 51.98, H, 7.82; N, 6.73%); δ(360 MHz; D$_2$O) 1.30–1.41 (1H, m, 0.5×CH$_2$); 1.54–1.72 (3H, m, 1.5×CH$_2$); 2.41–2.48 (1H, m, C$\underline{H}$—C—CO$_2$Me); 2.78–2.87 (5H, m, C$\underline{H}$—CO$_2$Me and 2×CH$_2$—N); 3.05–3.20 (2H, m, C$\underline{H}_2$—C—CO$_2$Me) and 3.68 (3H, s, CO$_2$Me).

(e) endo and exo-6-[5-(3-Amino 1,2,4-oxadiazol)-yl]-1-azabicyclo[3.2.1]octane

These were prepared from 6-carbomethoxy-1-azabicyclo [3.2.1]octane and hydroxyguianidine sulphate as described in Example 1, heating the sodium ethoxide reaction mixture for 16 hr. The crude product was purified by chromatography through alumina using dichloromethane/methanol (19:1) as eluent to give a white crystalline solid. Recrystallisation of the product from isopropyl alcohol/hexane gave 6-[5-(3-amino-1,2,4-oxadiazol)-yl-1-azabicyclo[3.2.1] octane (isomer A) as a white crystalline solid, mp 156°–158°: (Found: C, 53.17; H, 7.37; N, 27.57. C$_9$H$_{14}$N$_4$O.0.5H$_2$O requires C, 53.20; H, 7.39; N, 27.59) δ(360 MHz, CDCl$_3$) 1.40–1.96 (4H, m, 2×CH$_2$); 2.55 (1H, br s, C$\underline{H}$); 2.70–3.00 (4H, m, 2×CH$_2$); 3.10–3.40 (3H, m, CH$_2$ and CH); 4.40 (2H, br s, NH$_2$); m/e 194 (M$^+$).

Repeated recrystallisation of the product obtained from the filtrate of the initial recrystallisation gave a pure sample of 6-[5-(3-amino-1,2,4-oxadiazol)-yl]-1-azabicyclo [3.2.1] octane, (isomer B) mp 190°–195° (isopropyl alcohol): (Found: C, 53.11; H, 7.36; N, 27.53. C$_9$H$_{14}$N$_4$O. 0.5H$_2$O requires C, 53.20; H, 7.39; N, 27.59%]; δ(360 MHz, CDCl$_3$) 1.20–1.80 (4H, m, 2×CH$_2$); 2.60 (1H, br s, C$\underline{H}$): 2.80–3.00 (5H, m, 2×CH$_2$ and C$\underline{H}$-oxadiazole); 3.43 (2H, br s, CH$_2$—N); 4.34 (2H, br s, NH$_2$).

EXAMPLE 20

3-[5-(3-Amino-1,2,4-oxadiazol-yl]pyrrolidine hydrochloride (a) 1-Benzyl-3-hydroxymethylpyrrolidine This was prepared from itaconic acid and benzylamine by the procedure described by Feldkamp et al. J. Am. Chem. Soc.. (1961). 1519.

(b) 1-Benzyl-3-carboethoxypyrrolidine

1-Benzyl-3-hydroxymethylpyrrolidine was oxidised to 1-benzyl-3-carboethoxypyrrolidine by a procedure described by Rapoport (J. Org. Chem.. (1974), 39, 893) for the oxidation of 1-methyl-3-hydroxymethylpyrrolidine to the corresponding methyl ester. The crude product did not require further purification. δ(60 MHz, CDCl$_3$) 1.20 (3H, t, J=6.5 Hz, Me): 1.90–3.20 (7H, m, 33× CH$_2$ and C $\underline{H}$—CO$_2$Et); 3.60 (2H, s, C$\underline{H}_2$—N); 4.10 (2H, q, J=6 Hz, Me-C$\underline{H}_2$) and 7.25 (5H, m, C$_6$H$_5$).

(c) 3-Carboethoxypyrrolidine

A solution of 1-benzyl-3-carboethoxypyrrolidine (2 g, 8.6 mmol) in ethanol (75 ml) was subjected to hydrogenolysis over Pd(OH)$_2$ on a parr shaker for 48 hr. The catalyst was filtered off, the solvent removed under vacuum, and the residue chromatographed through alumina using dichloromethane/methanol (85:15) as eluant, to give the title product as a clear liquid (0.6 g); δ(60 MHz, CDCl$_3$) 1.20 (3H, t, J=7 Hz, OCH$_2$C$\underline{H}_3$); 1.70–2.30 (2H, m, CH$_2$); 2.50–3.20 (5H, m, 2×C$\underline{H}_2$—N, and C$\underline{H}$—CO$_2$Et); 4.10 (2H, q, J=7 Hz, OC$\underline{H}_2$CH$_3$).

(d) 3-[5-(3-Amino-1,2,4-oxadiazol)-yl]pyrrolidine hydrochloride

This was prepared from 3-carboethoxypyrrolidine and hydroxy guanidine sulphate by the procedure described in Example 1. The crude product was chromatographed through alumina using dichloromethane/MeOH (10:1) as eluant, to afford the title amino-oxadiazole as a clear oil. Addition of ethereal hydrogen chloride to a solution of the product in ether/MeOH (3:1) gave the hydrochloride salt; mp 168°–172° (isopropylalcohol). (Found: C, 36.80; H, 5.60; N, 27.90; Cl, 17.69. C$_6$H$_{11}$N$_4$O Cl. 0.4H$_2$O requires C, 36.42; H, 5.96; N, 28.32; Cl, 17.95%); δ(360 MHz, D$_2$O) 2.00–2.50 (2H, m, CH$_2$); 2.80–3.60 (5H, m, 2×CH$_2$ and CH).

EXAMPLE 21A endo-6[5-3-Methyl-1,2,4-oxadiazol)yl]-2-azabicyclo [2.2.2] octane (a) endo and exo-2-Benzyloxycarbonyl-6-methoxycarbonyl-2-azabicyclo[2.2.2]oct-7-ene Sodium borohydride (5.7 g, 0.15 mmol) was added portionwise to a solution of anhydrous pyridine (12.1 ml, 0.15 mmol) in methanol (100 ml), at -65° C. The mixture was cooled to -70° C. and benzylchloroformate (24.8 ml, 0.15 mmol) added dropwise, and stirred for 1 hr. The mixture was warmed slowly to room temperature, the solvent removed in vacuo and the residue taken up into water (40 ml) and extracted into ether (2×50 ml). The ethereal extracts were washed with 0.1N hydrochloric acid (10 ml) and water (3×10 ml). dried (MgSO$_4$) and evaporated. The residue was dissolved in acetonitrile (90 ml) and methyl acrylate (13.25 g, 0.154 mmol) and hydroquinone (1.0 g) added. The reaction mixture was heated at reflux for 6.5 days, the solvent removed under vacuum and the residue chromatographed through silica gel, eluting with toluene/ethyl acetate (10:1) to give a mixture of endo and exo products. The mixture was subjected to chromatography through alumina using dichloromethane as eluant to give the endo-Diels Alder product (6.03 g) and exo-adduct (1.72 g) as separated components. δ endo-(360 MHz, CDCl$_3$) 1.80–1.90 (2H, m, CH$_2$); 2.81–3.38 (4H, m, CH$_2$ and 2×CH); 3.65 (3H, s, OMe); 5.05–5.20 (3H, m, CH$_2$—N, and C$\underline{H}$); 6.25–6.35 (1H, m, vinyl H); 6.35–6.48 (1H, m, vinyl H); 7.30–7.42 (5H, m, C$_6$H$_5$). δ exo (360 MHz, CDCl$_3$); 1.50–1.60 (1H, m, CH); 2.05–2.15 (1H, m, CH); 2.52–2.58 (1H, m, CH); 2.75–2.80 (1H, m, CH); 3.00–3.12 (1H, m, CH); 3.36–3.48

(1H, m, CH); 3.65 (3H, s, CO₂Me); 4.93–5.10 (3H, m, C H₂—N and CH) and 7.25–7.38 (5H, m, C₆H₅).

(b) endo-6-Carbomethoxy-2-azabicyclo[2.2.2]octane

A solution of endo-2-benzyloxycarbonyl-6-carbomethoxy-2-azabicyclo[2.2.2]oct-7-ene (3.56 g, 11.8 mmol) in methanol (35 ml) was subjected to hydrogenation over Pd/C (0.35 g), at atmospheric pressure for 2 hr. The catalyst was filtered and the solvent removed in vacuo to afford the title ester as a clear oil (1.98 g). The oxalate salt was prepared: mp 109°–110° (dichloromethane): (Found: C, 48.53, H, 5.97, N, 4.62. C₉H₁₅NO₂ 1.3 H₂C₂O₄ requires C, 48.66, H, 6.19; N, 4.89%); δ(360 MHz, D₂O) 1.71–2.10 (7H, m, 3×CH₂ and CH); 3.15–3.28 (3H, m, CH₂—N, and CH—CO₂Me); 3.75 (3H, s, CO₂Me) and 3.81 (1H, br s, C H—N).

(c) endo-6[5-(3-Methyl-1,2,4-oxadiazol)yl]-2-azabicyclo [2.2.2]octane

This was prepared from acetamideoxime and endo-6-carbomethoxy-2-azabicyclo[2.2.2]octane by the procedure described for Example 18. The crude product was chromatographed through alumina using dichloromethane/methanol (19:1) as eluant to give the title endo-methyloxadiazole as a clear liquid. The hydrochloride salt was prepared, mp 215°–216° (isopropylalcohol/ether); (Found: C, 51.81, H, 6.87; N, 18.32. C₁₀H₁₅N₃O.HCl requires C, 52.28; H, 7.02; N, 18.29%); δ(360 MHz, D₂O) 1.80–2.05 (4H, m, 2×CH₂); 2.10–2.30 (2H, m, CH₂); 2.25–2.40 (1H, m, CH); 2.40 (3H, s, Me); 3.34 (2H, s, CH₂—N); 3.82–3.92 (1H, m, C H-oxadiazole) and 3.80–3.95 (1H, m, CH—N).

EXAMPLE 21B exo-6[5-(3-Methyl-1,2,4-oxadiazol)yl]-2-azabicyclo[2.2.2] octane (a) exo-6-carbomethoxy-2-azabicyclo[2.2.2]octane A solution of exo-2-benzyloxycarbonyl-6-carbomethoxy-2-azabicyclo[2.2.2]oct-7-ene (1.02 g, 3.4 mmol) in methanol (20 ml) was hydrogenated over Pd/C (1.0 g) at atmospheric pressure, for 12 hr. The catalyst was filtered and the solvent removed under vacuum to give the title saturated ester as a yellow liquid (0.29 g). The hydrochloride salt was prepared, mp 157°–158° (isopropylalcohol/ether); (Found: C, 52.43, H, 7.73; N, 6.34. C₉H₁₅NO₂ HCl requires C, 52.55, H, 7.84; N, 6.80); δ(360 MHz, D₂O) 1.60–1.85 (4H, m, 2×CH₂); 1.99–3.06 (4H, m, 2×CH and CH₂); 3.24 (2H, br s, CH₂—N); 3.78 (3H, s, CO₂ Me) and 3.75–3.90 (1H, m, C H—N).

(b) exo-6-[5-(3-Methyl-1,2,4-oxadiazol)-yl]-2-azabicyclo [2.2.2]octane

This was prepared from acetamideoxime and exo-6-carbomethoxy-2-azabicyclo[2.2.2]octane by the procedure described for Example 18. The crude product was purified by chromatography through alumina using dichloromethane/methanol (10:1) as eluant to give the desired exo-methyl oxadiazole as a yellow liquid. The hydrochloride salt was prepared, mp 183°–185° (isopropyl alcohol/ether); (Found: C, 52.23; H, 6.96; N, 18.20. C₁₁H₁₅N₃O.HCl requires C, 52.28; H, 7.02; N, 18.29% ]δ(360 MHz, D₂O ) 1.70–2.10 (2H, m, CH₂); 2.10–2.40 (4H, m, 2×CH₂); 2.45 (3H, s, Me); 2.32–2.50 (1H, m, CH); 3.29 (2H, br s, CH₂—N): 3.60–3.79 (1H, m, CH-oxadiazole) and 3.93–4.10 (1H, m. CH—N).

EXAMPLE 22

3-[5-(3-Ethoxycarbonyl-1,2,4-oxadiazol)-yl]quinuclidine Hydrochloride

Methyl 3-quinuclidinyl carboxylate hydrochloride (9.3 g, 45.2 mmol) was heated under reflux in concentrated hydrochloric acid (100 ml) for 16 hours. The reaction was concentrated under reduced pressure and the residue heated under reflux in thionyl chloride (150 ml) for 2.5 hours. The solution was concentrated in vacuo and the remaining solid suspended in dry tetrahydrofuran (150 ml) under a nitrogen atmosphere. Ethoxy-carbonyl formamide oxime (7.8 g, 59.0 mmol), prepared by the method of Warburton et al (J. Chem. Soc. (C), 1522, (1966)), in tetrahydrofuran (150 ml) was added dropwise and the reaction was stirred for 16 hours. The solution was evaporated under reduced pressure and the residue dissolved in water which was made basic with K₂CO₃. The solution was extracted with CH₂Cl₂ (3×) and the combined extracts dried (MgSO₄) and evaporated in vacuo. The residue was dissolved in dry dioxan (200 ml) and heated under reflux over type 4A molecular sieves (70 g) for 24 hours. The reaction was filtered and concentrated under reduced pressure to give a residue which was treated with ethereal HCl to give, after recrystallisation from propan-2-ol, the title compound: mp 170°–171° C.; (Found: C, 49.90; H, 6.31; N, 14.61. C₁₂H₁₇N₃O₃. HCl requires C, 50.09; H, 6.31; N, 14.61%) ν_max (nujol) 1748 cm⁻¹ (C=O): m/e 251 (M⁺ of free base): δ(360 MHz, D₂O) 1.42 (3H, t, J=7.2 Hz, CH₃), 1.80–2.01 and 2.10–2.28 (each 2H, each m, 5CH₂ and 8CH₂), 2.68–2.73 (1H, m, 4CH), 3.34–3.52 (4H, m, 6CH₂ and 7CH₂), 3.88 (2H, d, J=8.2 Hz, 2CH₂), 4.00–4.08 (1H, m, 3CH) and 4.52 (2H, q, J=7.2 Hz, OCH₂).

EXAMPLE 23

1-Methyl-3-[5-3-amino-1,2,4-oxadiazol)-yl]pyrrolidine

This was prepared from 1-methyl-3-methoxy carbonylpyrrolidine (336 mg, 2.35 mmol), hydroxy-

EXAMPLE 23

1-Methyl-3-[5-(3-amino-1,2,4-oxadiazol)-yl]pyrrolidine

This was prepared from 1-methyl-3-methoxy carbonylpyrrolidine (336 mg, 2.35 mmol), hydroxyguanidine sulphate (1.88 g, 14.1 mmol), and sodium (621 mg, 25.8 mmol) in absolute ethanol (50 ml) exactly as described in example 1. The crude product was purified by chromatography on alumina in 5% methanol in dichloromethane and then recrystallised from isopropanol-petroleum ether to afford the desired aminooxadiazole (140 mg) mp 62°–65°; (found: C, 50.52; H, 7.27; N, 33.25. C₇H₁₂N₄O requires C, 50.00; H, 7.14; N, 33.33%); m/e 168 (M⁺); δ(360 MHz, CDCl₃) 2.14–2.23 and 2.27–2.35 (each 1H, each m, 2×CH); 2.39 (3H, s, NCH₃); 2.58–2.65 (2H, m, NCH₂): 2.76–2.81 and 2.90–2.95 (each 1H, each m, 2×NCH); 3.46–3.55 (1H, m, 3-CH) and 4.37 (2H, broad, s, NH₂).

EXAMPLE 24

3-[5-(3-Amino-1,2,4-oxadiazol)-yl]-1-azabicyclo[2,2,1] heptane a) 1-Benzyl-3-ethoxycarboylpyrrolidine A solution of 1-benzyl-3-hydroxymethylpyrrolidine (60 g. 0.314 mol; J. Org. Chem., (1961), 26, 1519) in conc. sulphuric acid (7.3 ml) and water (350 ml) was treated at 0° with a solution of chromium trioxide (26.2 g) in conc. sulphuric acid (18 ml) and water (410 ml). The mixture was stirred at 0° for 5 min, 100° for 2 min and then cooled back to 0°. A further charge of the chromium trioxide solution was then added and the mixture heated at 100° for 0.5 h. After cooling again to 10°, excess sodium metabisulphite was added to destroy any remaining oxidant and the pH adjusted to 10 with 6N-sodium hydroxide solution. After filtration, the mixture was acidified to pH 2 with 6N-hydrochloric acid and the solution evaporated. The rigorously dried residue was treated at 20° for 16 h with anhydrous ethanol saturated with hydrogen chloride. The gum after evaporation of the solvent was partitioned between dichloromethane and water made basic with excess potassium carbonate and the required ethyl ester isolated from the organic layer (25 g): δ(60 MHz, CDCl₃) 1.20 (3H, t, J=6.5 Hz, CH₃); 1.9–2.2 (5H, m, 2×CH₂ and CH); 3.60 (2H, s, CH₂Ph); 4.10 (2H, q, J=6.5 Hz, CH₂CH₃) and 7.23 (5H, broad 2, C₆H₅).

b) 1-Ethoxycarbonylmethyl-3-ethoxycarbonylpyrrolidine

The foregoing 1-benzylpyrrolidine (18 g) in ethanol (400 ml) was subjected to hydrogenolysis over Pd(OH)₂ (5 g) at 50 psi in a Paar shaker for 72 h. After filtration, the solvent was evaporated and the resulting oil purified by chromatography on alumina in methanol-dichloro-methane (1:19) to give 3-ethoxycarbonyl-pyrrolidine (8 g) as a colourless oil. This amine (7.75 g, 54 mmol) in ether (70 ml) was treated at 0° with a solution of ethyl bromoacetate (4.53 g, 27 mmol) in ether (40 ml) in the presence of solid potassium carbonate (5 g). After 0.5h at 0° and 1 h at reflux, the precipitated solid was removed by filtration and the residue isolated from the filtrate purified by chromatography on alumina in dichloromethane to give the diester (5.56 g); δ(60 MHz, CDCl₃) 1.25 (6H, t, J=7 Hz, 2×CH₃); 2.1–3.2 (7H, m, 3×CH₂ and CHCO); 3.3 (2H, s, CH₂CO) and 4.15 and 4.20 (each 2H, each q, each J=7 Hz, 2×OCH₂).

c) 1-Azabicyclo[2,2,1]heptan-3-one

A mixture of ethanol (4.5 ml) and toluene (6 ml) was added dropwise to a rapidly stirred suspension of potassium (2.66 g, 68.2 mmol) in toluene (15 ml) at 120° under nitrogen. After 1 h at this temperature, a solution of the foregoing diester (6.24 g, 27.3 mmol) in toluene (25 ml) was then added and the mixture heated at 140° for 3 h. Concentrated hydrochloric acid (90 ml) was added, the two solvent phases separated and the aqueous phase heated under reflux for 18 h. The reaction mixture was evaporated to half volume, neutralised with solid potassium carbonate and extracted with dichloromethane. The material isolated from the organic extracts was chromatographed on silica in methanol-dichloromethane (1:9) to give the required azabicycle (250 mg), δ(CDCl₃, 360 MHz) 1.75–1.80 (1H, m, H of CH₂); 2.06–2.12 (1H, m, H of CH₂); 2.70–2.81 (4H, m, 2×NCH₂) and 3.00–3.12 (3H, m, COCH₂ and CH).

d) 3-(1,3-Dithian-2-ylidene)-1-azabicyclo-[2,2,1]heptane

A solution of n-butyl lithium in hexane (1.4 ml of a 1.6M solution; 2.3 mmol) was added to a solution of 2-trimethylsilyl-1,3-dithiane (457 mg, 2.37 mmol) in tetrahydrofuran (5 ml) stirred under nitrogen at −35° After 1.5 h, the foregoing ketone (220 mg, 1.98 mmol) in tetrahydrofuran (5 ml) was added and the mixture allowed to warm to 20° over 1 h. Water (20 ml) was added and the solution extracted with dichloromethane. Chromatography of the material isolated from the organic extracts on alumina in methanol-dichloromethane (1:49) gave the dithioacetal ketene (370 mg), a (CDCl₃, 360 MHz) 1.35–1.48 (1H, m, CH); 1.76–1.90 (2H, m, CH₂); 2.10–2.17 (2H, m. CH₂); 2.43 (1H, dd, J=3 Hz and 9 Hz, bridge 2.46–2.58 (1H, m, CH); 2.62 (1H, m, CHN); 2.70–2.94 (5H, m, CH and 2×CH₂S); 3.02 (1H, dd, J=3 Hz and 18 Hz, CH—C=C) and 3.41 (1H, dd, J=3 Hz and 18 Hz, CH—C=C).

e) 3-Ethoxycarbonyl-1-azabicyclo[2,2,1]heptane

The foregoing vinyl dithiane (370 mg, 1.74 mmol) in ethanol (30 ml) saturated with anhydrous hydrogen chloride was stirred at 50° for 16 h. After evaporation of the solvent, the residue was partitioned between dichloromethane and water to which solid potassium carbonate was added to pH 10. Chromatography of the residue isolated from the organic layer on alumina in methanol-dichloromethane (1:19) gave the required ethyl ester (227 mg), δ(CDCl₃ 360 MHz) 1.25 (3H, t, J=7 Hz, CH₃); 1.8–3.3 (10H, m, 4×CH₂ and 2×CH); 4.12 (2H, q, J=7 Hz, OCH₂).

f) 3-[5-(3-Amino-1,2,4-oxadiazol)-yl]-1-azabicyclo[2,2,1)]-heptane and hydrochloride salt Sodium metal (210 mg, 9.1 mmol) was added to a suspension of powdered molecular sieve (2 g) in ethanol (25 ml) stirred under nitrogen at 20°. Hydroxyguanidine hemisulphate hemihyrate (700 mg, 2.6 mmol) was then added and the mixture stirred for 15 min. After addition of a solution of the foregoing ester (220 mg, 1.3 mmol) in ethanol (3 ml), the mixture was heated under reflux for 3.5 h. After removal of the molecular sieve by filtration, the solvent was evaporated and the residue partitioned between dichloromethane and water. The material isolated from the organic layer was purified by chromatography on alumina in dichloromethane-methanol (24:1) followed by crystallisation from i-propanol-hexane (60 mg) as a mixture of exo and endo isomers, mp. 126°–127°; (found: C, 53.0; H, 6.7; N, 30.4. C₈H₁₂N₄O. 0.1 H₂O requires C, 52.8; H, 6.7; N, 30.8%); m/e 180 (M⁺); δ(CDCl₃, 360 MHz) 1.27 (1H, broad s, CH of CH₂); 1.66–1.78 (1H, m, CH of CH₂); 2.39–3.40 (8H, m, 3×CH₂ and 2×CH) and 4.37 (2H, broad 2, NH₂).

Chromatography of the mixture of isomers (through silica gel) using dichloromethane/methanol (2:1) as eluant gave the two separated isomers as white crystalline solids. Isomer A the least polar and major component was treated with ethereal hydrogen chloride to give the salt, mp. 230°–232° (methanol/ether), [Found: C, 44.54; H, 5.72; N, 25.42 C₈H₁₃N₄OCl requires C, 44.34; H, 6.00; N, 25.87%]δ(360 MHz, D₂O) 1.94–2.08 (1H, m, CH of CH₂); 2.22–2.31 (1H, m, CH of CH₂); 3.30–3.85 (8H, m, 2×CH₂—N) and 4.8–4.9 (2H, brs, NH₂); m/e 180 (M⁺). Isomer B Ethereal hydrogen chloride was added to isomer B to give the salt, mpt 214°–216° (methanol/ether); [Found C, 44.50; H, 5.81; N, 25.46. C₈H₁₃N₄OCl requires C, 44.34; H, 6.00; N, 25.87%] δ(360 MHz: D₂O ) 1.65–1.74 (1H, m, CH of CH₂); 2.08–2.15 (1H, m, CH of CH₂); 3.36–3.57 (5H, m, CH and 2×CH₂—N); 3.66–3.71 (1H, m 1×CH of CH₂-N); 3.86–4.01 (1H, m, CH-oxadiazole) and 4.02–4.07 (1H, m, 1×CH of CH₂—N); m/e 180 (M⁺).

EXAMPLE 25

1-Methyl-3[5-(3-amino-1,2,4-oxadiazol)-yl]-1,2,5,6-tetrahydropyridine

Hydroxyguanidine hemisulphate hemihydrate (6.65 g, 50 mmol) was stirred with molecular sieve (type 4A, log) in ethanol (50 ml) for 0.5 h. Sodium (2.2 g, 95 mmol) was then added, stirring continued for a further 0.5 h when all the sodium had dissolved, and then arecoline hydrobromide (2.3 g, 10 mmole) added to the reaction mixture. After 0.5 h at 20°, the mixture was heated under reflux for 0.5 h, cooled and neutralised by the addition of acetic acid (5.7 g). After filtration, the filtrate was evaporated and the residue taken into the minimum quantity of saturated aqueous potassium carbonate solution. Exhaustive extraction of this solution with dichloromethane followed by evaporation of the combined organic extracts gave the crude product which was purified by chromatography on alumina in ethyl acetate and then ethyl acetate-methanol (99:1). Evaporation of the single component fractions gave the required oxadiazole (310 mg), mp. 118°–119°; (Found: C, 53.3; H, 6.8; N, 30.6. C₈H₁₂N₄O. 0.05H₂O requires C, 53.0; H, 6.7; N, 30.9%); m/e 180 (M⁺); δ(CDCl₃, 360 MHz) 2.45 (5H, broad s, NCH₂ and NCH₃); 2.58 (2H, t, J=5.7 Hz, NCH₂CH₂); 3.30–3.32 (2H, m, CH₂CH); 4.39 (2H. broad s, NH₂) and 6.99–7.01 (1H, m, CH).

EXAMPLE 26

1-Methyl-3[5-(3-amino-1,2,4-oxadiazol)-yl]piperidine

This was prepared from ethyl 1-methyl piperidine-3-carboxylate using the procedure given in example 25. After chromatography the required oxadiazole was crystallised from ethyl acetate-hexane, mp 72°–73°; (Found: C, 50.4;H, 8.0; N, 29.2 $C_8H_{14}N_4O$. 0.4 $H_2O$ requires C, 50.7; H, 7.9; N, 29.6%); m/e 182 ($M^+$): a ($CDCl_3$, 360 MHz) 1.57–1.82 (4H, m, $CH_2CH_2$); 1.95–2.12 (2H, m, $NCH_2$); 2.32 (3H, s, $NCH_3$); 2.69–2.78 (1H, m, CH): 3.01–3.13 (2H, m, $NCH_2$) and 4.30 (2H, broad s,

EXAMPLE 27

6-[5-(3-Methyl-1,2,4-oxadiazol)-yl]-1-azabicyclo[3.2.1]octane Hydrochloride

This was prepared from 6-carbomethoxy-1-aza-bicyclo[3.2.1]octane and acetamideoxime according to the procedure described for example 18. The hydrochloride salt had mp. 240°–242° C. (isopropyl-alcohol); (Found: C, 52.53; H, 6.93;N, 18.14; $C_{10}H_{16}N_3O$ Cl requires C, 52.29;H. 6.97; N, 18.30%); δ(360 MHz, $CDCl_3$). 1.50–1.90 (4H, m, 2×$CH_2$); 2.36 (3H, s, Me); 2.62 (1H, br s, C$\underline{H}$-bridgehead); 2.80–2.94 (4H, m, 2×$CH_2$—N); 3.09 (1H, dd, J=5.4; 13 Hz, C $\underline{H}$—N); 3.42–3.50 (1H, m, C$\underline{H}$—N); 3.66 (1H, dd, J=5.4, 8.6 Hz, C$\underline{H}$-oxadiazole).

EXAMPLE 28

2[5-3-Amino-1,2,4-oxadiazol)-yl]quinuclidine

Crushed molecular sieve (10 g) and hydroxy-guanidine hemisulphate hemihydrate (7.98 g, 60 mmole) were stirred together in absolute ethanol (40 ml) under nitrogen for 0.5 h. Sodium 12.53 g, 110 mmol) was added in portions and stirring continued until all the metal had dissolved. Ethyl quinuclidine-2-carboxylate 11.83 g, 10 mmol) was added and the mixture stirred at 20° for 0.5 h and then at reflux temperature for 1 h. After cooling and filtering, the solution was evaporated and the residue partitioned between dichloromethane and a small amount of water. The material isolated from the organic layer was purified by chromatography or alumina in methanol-dichloromethane (3:97) and then recrystallised from ethyl acetate-hexane to afford the aminoxadiazole (280 mg), mp. 173°–175°; (Found: C, 55.7;H, 7.2; N, 28.7 $C_9H_{14}N_4O$ requires C, 56.0;H, 7.3;N, 29.0%); δ($CDCl_3$, 360 MHz) 1.52–1.71 (4H, m, 2×$CH_2$); 1.91–1.95 (1H, m, 4-CH); 2.00–2.04 (2H, m, $CH_2$); 2.81–3.12 (4H, m, 2×$NCH_2$); 4.09 (1H, overlapping dd, each J=8.6 Hz, 2-CH) and 4.39 (2H, broad s, $NH_2$).

EXAMPLE 29

3-Hydroxy-3[5-3-amino-1,2,4-oxadiazol-yl]quinuclidine

This was prepared from methyl 3-hydroxy-quinuclidine-3-carboxylate using the procedure given in example 25, except that the reaction time was 15 min. After filtration of the mixture and evaporation of the filtrate, the resulting solid was immediately purified by chromatography on alumina in methanol-dichloromethane (1:19) to give the desired aminoxadiazole (220 mg), mp 216°–217°; (Found: C, 50.8; H, 6.6; N, 26.8. $C_9H_{14}N_4O_2$. 0.1$H_2O$ requires C, 51.1; H, 6.7; N, 26.5%); δ($d_6$-DMSO, 360 MHz) 1.16–1.20, 1.27–1.36, 1.42–1.53 and 1.93–2.02 (each 1H, each m, 2×$CH_2$); 2.11 (1H, broad s, 4-CH); 2.54–2.74 (4H, m, 2×$NCH_2$); 2.77 and 3.48 (each 1H, each d, J=14 Hz, 2×NCH); 5.97 (1H, s, OH) and 6.26 (2H, broad s, $NH_2$).

EXAMPLE 30

2-[5-(3-Methyl-1,2,4-oxadiazol)-yl]-7-azabicyclo[3,2,1]oct-2-ene Hydrochloride (a) 2-Carbomethoxy-7-aza-8-oxotricyclo [4.2.1.0$^{3,7}$]nonane. Hydrochloride The free base (2 g, 0.01 mol) was prepared by the procedure described by Tufariello (J. Amer. Chem. Soc., (1979), 101, 2435), and dissolved in anhydrous ether (50 ml) at 0° C. Addition of 1.1 equiv of HCl dissolved in ether afforded a dense white precipitate. Filtration and recrystallisation from dichloromethane/ether afforded white crystals (1.8 g) mp 150° C.

(b) 2-Carbomethoxy-1-hydroxy-7-azabicyclo [3.2.1]octane

A solution of 1-carbomethoxy-7-aza-8-oxotricyclo [4.2.1.0$^{3, 7}$]nonane hydrochloride (1.5 g, 6.8 mmol) was dissolved in methanol (40 ml) to which was added a suspension of 10% palladium on charcoal (0.3 g) in methanol (5 ml). The resulting suspension was shaken under an atonosphere of hydrogen (45 psi) for 24 hours.

The catalyst was removed by filtration through celite and the solvent evaporated at reduced pressure. The residue was dissolved in water (20 ml), basified with 10% aqueous sodium carbonate, and extracted with dichloromethane (3×50 ml). The combined extracts were dried ($Na_2SO_4$) and evaporated, and the residue chromatographed through alumina using dichloromethane/methanol (95:5) an eluant to afford the title compound as a colourless oil (11 g) m/e 185 ($M^+$) δ(360 MHz, $CDCl_3$) 1.2–1.9 (6H, m, 3×$CH_2$); 2.85 (1H, dd, J 2.7, 5.9 Hz, C$\underline{H}$CO$_2$Me); 3.59 (1H, m, C$\underline{H}$N); 3.75 (3H, s, C$\underline{H}_3$); 3.85 (1H, m, C$\underline{H}$N) and 3.93 (1H, m, C $\underline{H}$OH).

(c) 2-[5-(3-Methyl-1,2,4-oxadiazol)-yl]-7-azabicyclo[3.2.1]oct-2-ene. Hydrochloride Activated molecular sieves (Type 4A, 1 g) were added to a stirred solution of acetamide oxime (1.0 g, 13.6 mmol) in anhydrous tetrahydrofuran (30 ml) under nitrogen. After 0.5 hr, sodium hydride (0.5 g of a 50% dispersion in oil, 11 mmol) was added and the solution stirred for a further 0.5 hour. A solution of 2-carbomethoxy-1-hydroxy-7-azabicyclo [3.2.1]octane (0.76 g, 4.1 mmol) in tetrahydrofuran (20 ml) was then added and the resulting mixture heated at reflux for 2 hours. The reaction mixture was then cooled to room temperature diluted with water (100 ml) and extracted with ethyl acetate (5×50 ml). The combined extracts were dried ($MgSO_4$), the solvent evaporated and the residue was chromatographed through alumina using dichloromethane/methanol (97:3) as eluant to afford a pale yellow oil (0.48 g). The product was further purified as the hydrochloride salt, mp. 239° (dec) (Ethanol); (Found: C, 52.3; H, 6.3; N, 18.3 $C_{10}H_{13}N_3O$.HCl requires C, 52.7; H, 6.2; N, 18.4%); m/e 191 ($M^+$of free base) δ(360 MHz, $D_2O$ ) 7.11 (1H, t, =C $\underline{H}$); 4.87 (1H, m, C$\underline{H}$), 4.37 (1H, m, C$\underline{H}$), 3.10 (1H, m, C $\underline{H}\underline{H}$ ); 2.64 (1H, m, CH$\underline{H}$); 2.42 (3H, s, C$\underline{H}_3$) and 2.4–1.95 (4H, m, 2×$CH_2$).

EXAMPLE 31

3-[5-(3-Chloro-1,2,4-oxadiazol)-yl]quinuclidine Hydrochloride

To a solution of 3-[5-(3-amino-1,2,4-oxadiazol)-yl] quinuclidine (4.0 g, 20 mmol) in concentrated hydrochloric acid (40 ml) at 0° C. was added dropwise sodium nitrite (2.0 g, 30 mmol) in water (1 ml). After complete addition the solution was stirred for 0.5 h. then filtered and concentrated under reduced pressure. The residue was treated with cold potassium carbonate solution which was extracted with dichloromethane. The dichloromethane solution was dried ($Na_2SO_4$) and then treated with ethereal HCl to give the title compound as a white solid (3.36 g); mp 179°–182° C.; (Found: C, 43.26; H, 5.29; N, 16.90. $C_9H_{13}Cl_2N_3O$ requires C, 43.22; H, 5.24; N, 16.80%); m/e 214 (FAB+, [M+H]$^+$of free base); δ(360 MHz, D₂O) 1.85–2.01 and 2.10–2.25 (each 2H, each m, 5CH₂ and 8CH₂), 2.66–2.72 (1H, m, 4CH), 3.35–3.52 (4H. m, 6CH₂ and 7CH₂); 3.77–3.90 and 3.95–4.02 (2H and 1H respectively, each m, 2CH₂ and 3CH).

EXAMPLE 32

5-[5-3-Methyl-1,2,4-oxadiazol-ylquinuclidine-3-one a) cis Piperidine-3,4-dicarboxylic acid-3-methyl ester hydrochloride Pyridine-3,4-dicarboxylic acid 3-methyl ester (5.00 g, 27.6 mmol), prepared by the method of J. C. S. Perkin I, 1981, 3012, in methanol (50 ml) was treated with excess ethereal hydrogen chloride and the solution evaporated to dryness. The resulting salt in methanol (100 ml) was hydrogenated over platinum oxide (500 mg) at 50 p.s.i. and ambient temperature until uptake ceased (24 h). The catalyst was removed by filtration through Hyflo and the filtrate evaporated to give the title compound (6.17 g, 100%), m.p. 180°–184° (dec) δ(360 MHz, D₂O ) 2.10–2.20 (2H, m, 5-CH₂); 3.19–3.25 (2H, m, 3-CH, 4-CH); 3.27–3.32 (1H, m, 6-CH ax); 3.34–3.39 (1H, m, 6-CH eq); 3.51 (1H,dd, J13 Hz and 4 Hz, 2-CH eq); 3.60 91H, dd, J 7.5 Hz and 13 Hz, 2-CH ax).

b) cis 1-t-Butoxycarbonylpiperidine-3,4-dicarboxylic acid 3-methyl ester

The foregoing piperidine salt (7.16 g, 32.1 mmol) was dissolved in a solution of sodium carbonate (6.80 g, 64.2 mmol) in water (50 ml) and a solution of di-t-butyl dicarbonate (8.39 g, 38.5 mmol) in dioxan (15 ml) added and stirred at room temperature 20 h. The solution was washed with ether, the aqueous layer acidified with 2M citric acid, then extracted twice with ethyl acetate. The extracts were washed in turn with water and brine, dried over magnesium sulphate and evaporated to give the product 7.78 g, 84%. m.p. 129°–136°; (Found: C, 54.32;H, 7.19: N, 4.94. $C_{13}H_{21}NO_6$ requires C, 54.35; H, 7.37; N, 4.88%): m/e (CI⁻) 286 (M-H⁻) γmax 3200 (br), 1740, 1700 (sl), 1655 cm¹δ(360 MHz, CDCl₃1.44 (9H, s, tBu); 1.89 (1H, br, 5-CH); 2.13 (1H, br, 5-CH); 2.84–2.89 (1H, m, 4-CH ); 2.93–2.96 (1H, m, 3-CH); 3.12–3.21 (1H, m, 6-CH ); 3.43–3.48 (1H, m, 6-CH); 3.68–3.75 (1H, m, 2-CH ); 3.69 (3H, s, OCH₃) 4.07–4.14 (1H, m, 2-CH).

c) Methyl-1-t-butoxycarbonyl-4-diazomethyl carbonylpiperidine-3-carboxylate

The foregoing piperidine monoester (5.0 g, 17.4 mmol) was added to a suspension of sodium hydride (0.57 g of 80% dispersion, 19.1 mmol) in dry tetrahydrofuran (50 ml) and stirred at 25° until gas evolution ceased (2 h). Thionyl chloride (2.28 g, 19.2 mmol) was added and the mixture heated to 60° for 1 h. The cooled mixture was added dropwise to an ice-cooled ethereal solution of diazomethane, generated from N-methyl-N-nitroso-p-toluene-sulphonamide (26.9 g, 125 mmol) by standard methods, and allowed to stand overnight. The solvent was evaporated, the residue partitioned between sodium hydrogen carbonate and dichloromethane, and the organic layer dried and evaporated. Column chromatography on silica in dichloromethane/ethyl acetate (4:1) afforded the pure diazoketone as a yellow gum (3.4 g, 63%). γmax 2120, 1740, 1690, 1640 cm⁻¹ δ(360 MHz, CDCl₃) 1.44 (9H, s, t-Bu); 1.76 (1H, br, 5-CH); 2.01–214(1H, m, 5-CH); 2.81 (1H, br) and 2.88–2.98 (1H, m, 3-CH and 4-CH); 3.22–3.34 (1H, m, 6-CH ); 3.50–3.71 (2H, m, 2-CH and 6-CH); 3.68 (3H, s, OCH₃); 4.02–4.11 (1H, m, 2-CH); 5.36 (1H, s, CH=N₂).

d) Methyl 5-oxoquinuclidine-3-carboxylate

To a solution of the foregoing diazoketone (529 mg, 1.70 mmol) in dichloromethane (25 ml) at 0° was added hydrogen bromide in acetic acid (1.0 ml of 48% w/v) and the solution stirred for 30 min. The solvent was removed using a toluene azeotrope to give methyl-4-bromomethylcarbonylpiperidine-3-carboxylate hydrobromide as a gum. δ(360 MHz, D₂O ) 2.01–2.22 (2H, m, 5-CH₂); 3.16–3.33 (2H, m, 3-CH, 4-CH); 3.40–3.58 (3H, m, 2-CH, 6-CH₂); 3.72–3.78 (1H, m, 2-CH); 3.73 (3H, s, OCH₃); 4.46 (2H, s, CH₂Br). This material in dry acetonitrile (200 ml) was added dropwise to boiling acetonitrile (500 ml) containing diisopropylethylamine (5.0 ml, 29 mmol) over 7 h, and refluxing continued for a further 1 h. The solvent was evaporated and the residue in 2M potassium carbonate extracted with dichloromethane. The extracts were dried, evaporated and purified by chromatography on silica in 5% methanol in dichloromethane to give the quinuclidine (120 mg, 39%) as an 80:20 mixture of diastereoisomers in which the R*R* configuration predominates. m/e 183 (M⁺). γmax 1740cm⁻¹. δ(360 MHz, CDCl₃) 2.01–2.07 (2H, m, 8-CH₂); 2.69 (1H, q, J 3 Hz, 4-CH); 2.88–2.97 (2H, m, 7-CH₂); 3.03–3.10 (1H, m, 3-CH); 3.14–3.25 (2H, m, 2-CH₂); 3.32 (1H, d, J 10 Hz, 6-CH); 3.39 (1H, d, J 10 Hz, 6-CH); 3.69 (3H, s, OCH₃).

e) 5-[5-(3-Methyl-1,2, 4-oxadiazol)yl]-quinuclidin-3-one

A solution of acetamide oxime (570 mg, 7.7 mmol) in dry THF (50 ml) containing powdered 4A molecular sieve (1.5 g) was stirred at 20° for 30 min, then sodium hydride (230 mg of 80% dispersion, 7.7 mmol) added. The mixture was heated to reflux for 15 min, cooled, and the foregoing quinuclidine ketoester (1.08 g, 5.9 mmol) in THF (10 ml) added. The solution was stirred for 15 min at 20°, then 1 h at reflux. The cooled mixture was filtered through Hyflo, the filtrate evaporated and partitioned between 2M potassium carbonate and dichloromethane. The organic layer was dried, evaporated and purified by chromatography on silica in 10% methanol in ethyl acetate, to give isomer A (first eluted) (127 mg) and isomer B (125 mg). Isomer A (R*S*) was recrystallised from ethyl acetate-ether, m.p. 85°–86.5°; (Found: C, 57.82; H, 6.23; N, 20.41. $C_{10}H_{13}N_3O_2$ requires C, 57.96; H, 6.32; N, 20.28%); m/e (CI) 208 (M+H⁺); γmax 1740 cm⁻¹. δ(360 MHz, CDCl₃) 1.84–1.96 (1H, m, 8-CH); 2.08–2.19 (1H, m, 8-CH); 2.43 (3H, s, CH₃); 2.87 (1H, q, a 3 Hz, 4CH); 2.89–3.00 (1H, m, 7-CH); 3.09–3.20 (1H, m, 7-CH); 3.39 (2H, s, 2-CH₂); 3,44 (1H, dd, J14 Hz and 2 Hz, 6-CH); 3.52 (1H, dd. J14 Hz and 6 Hz, 6-CH); 3.60–3.64 (1H, m, 5-CH).

Isomer B (R*R*) was recrystallised from ethyl acetate m.p. 94°–95° (Found: C, 58.04; H, 6.28; N, 20.50. $C_{10}H_{13}N_3O_2$ requires C, 57.96; H, 6.32; N, 20.28%); m/e (CI) 208 (M+HH⁺); γmax 1740; δ(360 MHz, CDCl₃); 2.08–2.24 (2H, m, 8-CH₂); 2.36 (3H, s, CH₃); 2.78 (1H, q, J3 Hz, 4-CH); 2.95–3.10 (2H, m. 7-CH₂); 3.32–3.38 (1H, m, 6-CH); 3.39 (1H, d. J19 Hz, 2-CH); 3.46–3.51 (1H, m, 6-CH): 3.51 (1H, d, J19 Hz, 2-CH); 3.66–3.72 (1H, m, 5-CH).

The intermediate methyl 5-oxoquinuclidine-3-carboxylate required in this preparation was also synthesised by the following sequence:

a) N,N-Diethyl 4-Methoxycarbonylpyridine 3-carboxamide

Sodium hydride (6.6 g of 80% dispersion, 0.22 mol) was washed with hexane, suspended in dry tetrahydrofuran (500 ml) under nitrogen and solid pyridine-3,4-dicarboxylic acid 4-methyl ester, (36.2 g, 0.Z0mol: prepared By the method of J. C. S. Perkin I, (1981) 3012) added portionwise. The mixture was stirred at 25° for 1 h, then at reflux for 30 min and cooled. Thionyl chloride (16.0 ml, 0.22 mol) was added and stirring continued at 25° for 1 h and at 70° for 30 min. The solution was cooled and diethylamine (43.8 g, 0.60 mol)

added. After standing overnight, 2M potassium carbonate was added and the product extracted with dichloromethane. Evaporation of the organic layers gave the ester amide as an orange oil (44.7 g) which was used in the next step without purification. m/e (CI) 237 (M+H⁺); δ(CDCl₃) 1.08 and 1.30 (each 3H, t, J7 Hz, 2×₂CH₃); 3.13 and 3.61 (each 2H, q. J7 Hz, 2×CH₂CH₃); 3.91 (3H, s, OCH₃); 7.82 (1H, d, J5 Hz, 5-CH); 8.61 (1H, s, 2-CH) and 8.75 (1H, d, J5 Hz, 6-CH).

b) N,N-Diethyl 4-Methoxycarbonyl-1-methoxycarbonylmethyl pyridinium-3-carboxamide bromide The foregoing pyridine ester amide (23.6 g, 0.10 mol) and methyl bromoacetate (15.3 g, 0.10 mol) were heated in methanol under reflux for 24 h and the solvent evaporated. The residue in water was washed with dichloromethane and the aqueous layer evaporated to dryness to give the desired pyridinium salt which crystallised on standing (36.9 g). m.p. 133°–134° (dec) δ(DMSO) 0.95 and 1.10 (each 3H, t. J7 Hz. 2×CH₂CH₃); 3.37 and 3.39 (each 2H, q, J7 Hz, 2×CH₂ CH₃); 3.70 and 3.84 (each 3H, s, 2×OCH₃); 5.67 (2H, s, CH₂CO₂); 8.56 (1H, d, J6 Hz, 5-CH); 9.20 (1H, d, J6 Hz, 6-CH); 9.31 (1H, s, 2-CH).

c) Cis N,N,Diethyl 4-Methoxycarbonyl-1-methoxycarbonylmethyl piperidine-3-carboxamide The foregoing crude pyridinium salt (36.0 g, 0.093 mol) was treated with Raney nickel in methanol (200 ml) to remove sulphur containing impurities and filtered. The filtrate was hydrogenated over platinum oxide (600 mg) at 50 psi and 50° until uptake ceased (72 h). The solution was filtered through Hyflo, evaporated and partioned between 2M potassium carbonate and dichloromethane. Chromatography of the residue from the organic layer on silica in 3% methanol in dichloromethane gave the desired piperidine (9.0 g) as an oil. m/e (CI) 315 (M+H⁺); δ(CDCl₃) 1.09 and 1.22 (each 3H, t, J7 Hz, 2×CH₂CH₃); 1.92–2.01 (1H, m, 5-CH ax); 2.25–2.34 (1H, m, 5-CH eq); 2.60–2.66 (2H, m, 4-CH, 6-CH); 2.75 (1H, dd, J4 Hz, 11 Hz, 3-CH); 2.84–2.90 (1H, m, 6-CH); 2.99 (1H, dd, J8 Hz, 11 Hz, 2-CH ax); 3.16–3.21 (1H, m, 2-CH, eq); 3.28–3.43 (6H, m, 2×CH₂CH₃, CH₂CO₂) and 3.66 and 3.70 (each 3H, s, 2×OCH₃.

d) Methyl 5-Oxoquinuclidine-3-carboxylate

A suspension of molten potassium (2.63 g. 67.5 mol) in dry toluene (70 ml) was heated in an oil bath at 120° whilst stirring vigorously with a Hirschberg stirrer, and methanol (3.0 ml. 73 mmol) was added dropwise. After 30 min, the bath temperature was raised to 140° and the foregoing piperidine (8.5 g, 27.0mol) in toluene (20 ml) added dropwise over 15 min. Heating and stirring was continued for 2 h, then mixture cooled in ice and concentrated hydrochloric acid (100 ml) added. The toluene layer was separated, washed with more hydrochloric acid (60 ml), and the combined acid layers heated under reflux for 16 h. The cooled solution was evaporated to dryness, using a toluene azeotrope, then the residue was suspended in methanol (400 ml) and dry hydrogen chloride passed in for 2 h. The solution was stirred at 25° for 2 days, filtered, evaporated and partitioned between 2M potassium carbonate and dichloromethane. Chromatography of the residue from the organic layer on silica in 2% methanol in dichloromethane yielded the desired keto ester (488 mg), identical in all respects with that obtained by the route given above.

EXAMPLE 33

5-[5-(3-Methyl-1,2,4-oxadiazol)-yl]quinuclidin-3-ol

To a solution of 4R*5S*5-[5-(3-methyl-1,2,4-oxadiazol)-yl]quinuclidin-3-one (isomer A) 400 mg. 1.93 mmol) in ethanol (20 ml) at 0° was added sodium borohydride (146 mg, 3.86 mmol) and the solution stirred for 1 h. Excess borohydride was destroyed with 2M hydrochloric acid, then the solution basified with 2M potassium carbonate and the product extracted with dichloromethane, dried and evaporated. Chromatography on alumina in 1% methanol in dichloromethane did not separate the two epimeric alcohols, but gave the title compound (270 mg) as a 4:36 mixture, H.P.L.C. retention times 6.60, 7.37 min on Spherisorb Cl in 50mM phosphate, 0.2% triethylamine, pH 6.5-acetonitrile 90:10. m.p. 112–114.5 (Found: C 56.87; H, 7.10;N, 19.57; C₁₀H₁₅N₃O₂0.1H₂O requires C, 56.91; H, 7.26; N, 19.91%): m/e (CI) 210 (M+H⁺); vmax 3500–2500 (br), 1575 cm⁻¹; δ(360 MHz, CDCl₃); 1.32–1.50 (1H, m, 8-CH); 1.68–1.98 (2H, m, 8-CH and OH); 2.29–2.34 (1H, m, 4-CH); 2.40 (3H, s, CH₃); 2.63–2.76 (2H, m, 7-CH₂); 2.88–2.97 (2H, m, 2-CH, 6-CH): 3.05–3.28 (3H, m, 2-CH, 5-CH, 6-CH); 4.03–4.09 (1H, m, 3-CH).

The 4R*5R* isomer of the starting quinuclidinone (381 mg, 1.84 mmol) was treated in exactly the same way to yield the title alcohol (284 mg) as 15:85 mixture, HPLC retention times 3.67, 4.04 min on Spherisorb-NH₂ in acetonitrile-water 80:20. m.p. 150°–155° (Found: C, 57.26; H, 7.04;N, 19.73; C₁₀H₁₅N₃O₂ requires C, 57.40;H, 7.23;N, 20.08%): m/e (CI) 210 (M+H⁺); vmax 3500–2500 (br), 1570 cm⁻¹; δ(360 MHz, CDCl₃); 1.55–1.64 (1H, m, 8-CH): 1.75–1.84 (1H, m, 8-CH); 2.38 (3H, s, CH₃); 2.54–2.59 (1H, m, 4-CH); 2.75–2.84 (3H, m, 7-CH₂, 6-CH); 3.12–3.49 (5H, m, 2-CH₂, 5-CH, 6-CH, OH); 3.88–3.92 (1H, m, 3-CH).

EXAMPLE 34

5-Methyl-3-[5-(3-methyl-1,2,4-oxadiazol)-yl]quinuclidine a) Methyl 5-Methylenequinuclidine-3-carboxylate Methyl triphenylphosphonium iodide (2.97 g, 7.35 mmol) and potassium t-butoxide (0.83 g, 7.35mol) in dry tetrahydrofuran (40 ml) was heated under reflux for 1.5 h, then cooled to 0° and methyl 5-oxo quinuclidine-3-carboxylate (see Example 3d) (1.17 g, 6.39mol) in tetrahydrofuran (5 ml) added. The mixture was stirred at 0° for 1 h, at 20° for 1 h then partitioned between 2M potassium carbonate solution and dichloromethane. The material obtained from the organic layer was purified by chromatography on silica in 5% methanol in dichloromethane to give the desired methylene quinuclidine as a colourless gum (0.746 g): m/e 181 (M⁺); δ(360 MHz, CDCl₃) 1.60–1.68 (1H, m, 8-CH); 1.78–1.87 (1H, m, 8-CH); 2.77–2.92 (1H, m, 7-CH); 2.82–2.85 (1H, m, 4-CH); 3.00–3.17 (2H, m, 3-CH, 7-CH); 3.26 (1H, d, J13 Hz, 2-CH); 3.43 (1H, dd J13 Hz, 5 Hz, 2-CH); 3.56 (2H, s, 6-CH₂): 3.75 (3H, s, OCH₃); 4.82 (1H, s, C=CH) and 5.13 (1H, s, C=CH).

b) Methyl 5-Methylquinuclidine-3-carboxylate

The foregoing methylene quinuclidine (745 mg, 4.12 mmol) in methanol (60 ml) was hydrogenated over 10% palladium on carbon (100 mg) at 50 p.s.i. and 25° until uptake ceased. Filtration through Celite and evaporation yielded the methyl quinuclidine (579 mg) as a mixture of two diastereoisomers, which was used in the next step without purification; m/e 183 (M⁺); δ(360 MHz, CDCl₃) 1.04 and 1.05 (each d, J7 Hz, CH₃); 1.36–1.45 (1H, m, 8-CH) 1.58–1.85 (2H, m, 5-CH, 8-CH); 1.91–1.95 (1H, m, 4-CH); 2.18–2.31 (1H, m, 3-CH); 2.66–3.33 (6H, m, 2-CH₂, 6-CH₂, 7-CH₂) and 3.71 and 3.72 (3H, each s, OCH₃), c) 5-Methyl-3[5- 3-methyl-1,2, 4-oxadiazol-yl]qinuclidine A solution of acetamide oxime (304 mg, 4.11 mmol) in dry tetrahydrofuran (30 ml) containing powdered 4A molecular sieve (1.0 g) was stirred for 1 h, sodium hydride (99 mg of 80% dispersion, 4.11 mmol) added, and the mixture heated under reflux for 15 min. After cooling to 25°, the foregoing methyl 5-methylquinuclidine-3-carboxylate (575 mg, 3.15 mmol) in tetrahydrofuran (9 ml) was added and stirring continued for 30 min at 25° and 40 min at reflux. The cooled solution was filtered through Celite, evaporated to dryness and partitioned between 2M potassium carbonate and dichloromethane. Chromatography of the material obtained from the organic layers on alumina in 2% methanol in dichloromethane yielded the title compound (340 mg) as a mixture of all four diastereoisomers, ratio 16:48; 11:25 by capillary g.c., 25 m BP10, 170°, RT 11.05, 11.17, 11.40, 11.89 min. The mixture was converted to the hydrochloride, mp 152°–158° (softens at 130 e); [Found: C, 52.9; H, 7.3;N, 16.3. $C_{11}H_{17}N_3O \cdot HCl_{0.45} H_2O$ requires C, 52.5; H, 7.6; N, 16.7%); m/e 207 ($M^+$, free base); $\delta$(360 MHz, $D_2O$) 0.62, 1.08, 1.20, 1.23 (3H, each d, J7 Hz, 5-$CH_3$); 1.91–1.96 (1H, m, 8-CH); 2.05–2.23 (1H, m, 8-CH); 2.41–2.50 (2H, m, 4-CH, 5-CH); 2.42 (3H, s, Ar $CH_3$); 2.82–2.96 (1H, m, 3-CH); 3.31–3.45 (2H, m,7-$CH_2$) and 3.59–4.08 (4H, m, 2-$CH_2$, 6-$CH_2$).

EXAMPLE 35

5-[5-3-Methyl-1,2, 4-oxadiazol)-yl]quinuclidine-3-carboxylic acid Hydrochloride a) 3-(1,3-Dithan-2-ylidene -5-[5-3-methyl-1,2,4-oxadiazol)yl]quinuclidine n Butyl lithium (5.5 ml of 1.5M solution, 8.29 mmol) was added to a stirred solution of 2-trimethylsilyl-1,3-dithian (1.59 g, 8.29 mmol) in dry tetrahydrofuran at -30° under nitrogen. After 1 h 5-[5-(3-methyl-1,2,4-oxadiazol)-yl] quinuclidine-3-one (see Example 32), as a mixture of diastereoisomers, (1.56 g, 7.54 mmol) in tetrahydrofuran (10 ml) was added, and after 20 min at –30°, the solution was allowed to warm to 25° over 1 h. Water (20 ml) was added, and extracted three times with dichloromethane. Chromatography of the material obtained from the organic extracts on silica in 5% methanol in ethyl acetate yielded one diastereoisomer ("A") of the pure product (80 mg) and the other as a mixture (712 mg). Diastereoisomer A (obtained pure) had m/e 309 ($M^+$); $\delta$($CDCl_3$) 1.48–1.57 (1H, m, 8-CH); 1.72–1.81 (1H, m, 8-CH); 2.15–2.22 (2H, quintet, J6 Hz, $SCH_2CM2$); 2.41 (3H, s, $CH_3$); 2.77–3.05 (7H, m, 4-CH, 7-$CH_2$, 2×$SCH_2$); 2.24–3.31 (1H, m, 6-CH); 3.37–3.43 (1H, m, 6-CH); 3.56 (2H, s, 2-$CH_2$) and 3.55–3.58 (1H, m, 5-CH).

b) Methyl 5-[5-3-Methyl-1,2,4-oxadiazol)-yl]quinuclidine-3-carboxylate

A solution of the foregoing dithian (88 mg, 0.28 mmol) in methanol saturated with hydrogen chloride (10 ml) was stirred at 25° for 24 h and the solvent evaporated. The residue in 2M potassium carbonate was extracted with dichloromethane. Chromatography of the residue from the organic extracts on silica in 5% methanol in dichloromethane gave the ester as a mixture of diastereoisomers (45 mg): [Found: CI mass spectrum: M-H⁻, 250.1192. $C_{12}H_{16}N_3O_3$ requires M-H⁻, 250.1192); m/e (CI) 251 ($M^+$). $\delta$1.43–1.51 (1H, m, 8-CH): 1.68–1.81 (1H, m, 8-CH); 2.40, 2.41 (3H, 2 x s, Ar $CH_3$); 2.57–2.62 (1H, m, 4-CH): 2.70–2.95 (4H, m, 3-CH, 5-CH, 7-$CH_2$); 3.13–3.41 (4H, m, 2-$CH_2$, 6-$CH_2$); 3.74, 3.76 (3H, 2×s, $OCH_3$), c) 5-[5-(3-Methyl-1,2,4-oxadiazol)-yl]quinuclidine-3-carboxylic acid. Hydrochloride The title compound was obtained as a mixture of diastereoisomers by treating the foregoing ester with 6M hydrochloric acid at 25° for 24 h followed by evaporating to dryness.

EXAMPLE 36

5-[5-3-Methyl-1,2, 4-oxadiazol) quinuclidine-2-carboxylic. Acid Hydrochloride a) Methyl-5-Methoxymethylenequinuclidine-2-carboxylate n-Butyllithium (13,67 ml of a 1.5M solution; 20.5 mmol) was added at 20° to a suspension of methoxymethyltriphenyl phosphonium chloride (7 g, 20.5 mmol) stirred in ether (150 ml) under nitrogen. After 2 h, the mixture was cooled to −35° and a solution of methyl 5-oxoquinuclidine-2-carboxylate (3 g, 16.4 mmol; prepared as described in Zhur. Obshchei. Khim., (1960), 30, 519;see Chem. Abs. (1960), 54: 24723) in ether (20 ml) added. The mixture was allowed to warm to 20° over 1 h and then stirred at this temperature for 16 h. After removing the precipitated triphenylphosphine oxide by filtration, the ether was evaporated off and the resulting oil subjected to chromatography on silica in 3% methanol in dichloromethane to afford the title compound (2.05 g) as a mixture of isomers: m/e 211 ($M^+$); $\delta$(360 MHz, $CDCl_3$) 1.2–2.0 (4H, m, 2×$CH_2$); 2.18–2.34 (1H, m, 4-CH); 2.5–3.4 (5H, m, 2×$NCH_2$ and NCH); 3.50–3.56 (3H, m, $OCH_3$); 3.78–3.82 (3H, m, $CO_2CH_3$) and 5.73–5.83 (1H, m, CH).

b) Methyl 5-Formylquinuclidine-2-carboxylate

The foregoing enol-ether (3.6 g) in chloroform (50 ml) was treated at 20° with perchloric acid (40 ml) for 3 h. The chloroform layer was discarded and replaced by dichloromethane (50 ml). Water (50 ml) and then solid sodium carbonate was added cautiously to the mixture until the pH reached 9.5. Evaporation of the organic phase gave the desired aldehyde, (2.76 g); [Found: (high resolution mass spectrum) $M^+=197.1057$ $C_{10}H_{15}NO_3$ requires $M^+=197.1052$]; $\delta$($CDCl_3$ 360 MHz) 1.5–2.6 (5H, m, 2×$CH_2$ and 4-CH); 2.8–3.6 (6H, m, 2×$NCH_2$, 2-CH and 5-CH); 3.75–3.81 (3H, m, $OCH_3$) and 9.75–9.81 (1H, m, CHO).

c) Methyl 5-[5-3-Methyl-1,2,4-oxadiazol)yl]quinuclidine-2-carboxylate

The foregoing aldehyde (1.18 g, 6 mmol) in 1M sulphuric acid (5 ml, 5 mmol) at 15° was treated with aqueous potassium permanganate solution (40 ml of a 0.1M solution, 4 mmol) added dropwise over 15 min. After a total time of 1 h, the reaction mixture was filtered through hyflo and the resulting aqueous solution freeze dried over 16 h. The resulting powder was heated under reflux in thionyl chloride (20 ml) for 3 h and then evaporated to dryness. Re-evaporation after the addition of toluene gave a gum which was taken up in dimethylformamide (10 ml) to which acetamide oxime (370 mg, 5 mmol) was added. After 1 h at 60° and 16 h at 120°, the reaction mixture was again evaporated to dryness and the residue partitioned between dichloromethane and water to which excess potassium carbonate was added. The material isolated from the organic layer was purified by chromatography on silica in 5% methanol in dichloromethane to afford the oxadiazole as a mixture of isomers (140 mg); [Found: (high resolution mass spectrum) $M^+=251$. 1268. $C_{12}H_{17}N_3O_3$ requires $M^+=251.1270$]; $\delta$($CDCl_3$, 360 MHz) 1.25–2.09 (4H, m, 2×$CH_2$); 2.28–2.54 (4H. m, $CH_3$ and 4-CH); 2.90–3.69 (6H, m. 2×$NCH_2$, 2-CH and 5-CH) and 3.77–3.82 (3H, m. $OCH_3$).

d) 5-[5-(3-Methyl-1,2,4-oxadiazole)-yl]quinuclidine-2-carboxylic Acid. Hydrochloride All of the foregoing ester was treated with 6N-hydrochloric acid at 25° for 16 h to give the title compound as a mixture of diastereomers.

EXAMPLE 37

5-[5-(3-Amino-1,2, 4-oxadiazol-yl]-quinuclidine-3-ol Hydrogen Oxalate a) 5-5-(3-Amino-1,2,4-oxadiazol-yl]-quinuclidine-3-one A suspension of hydroxyguanidine hemisulphate hemihydrate (1.15 g, 8.67 mmol) and powdered 4A molecular sieve (5 g) in ethanol (50 ml) was stirred for 1 h, then sodium (0.38 g, 16.7 mmol) was added, and the mixture heated under reflux for 20 min and cooled. A solution of methyl 5-oxoquinuclidine-3-carboxylate (1.22 g, 6.67 mmol) (see Example 32) in ethanol (15 ml) was added and stirred for 30 min at 25°, 30 min at reflux and recooled in an ice bath. Acetic acid (0.5 ml) was added and the solution filtered through Hyflo. The filtrate was basified with aqueous potassium carbonate and evaporated to dryness. The residue was extracted with ethanol and the solvent removed. Chromatography of the material obtained on silica in 10% methanol in dichloromethane yielded the amino oxadiazole (107 mg) as a 3:1 mixture of diastereoisomers; [Found: (Cl⁻ high resolution mass spectrum): $(M-H)^-=207°0869$; $\delta C_9H_{11}N_4O_2$ requires $(M-H)^-=207.0882$]; $\delta(CDCl_3)$ 2.08–2.14 (2H, m, 8-CH$_2$); 2.76–2.79 and 2.84–2.87 (1H, each m, 4-CH of two diastereoisomers); 2.93–3.08 (2H, m, 7-CH$_2$); 3.25–3.32 (1H, m, 6-CH); 3.36–3.52 (3H, m, 2-CH$_2$, 6-CH); 3.56–3.62 (1H, m, 5-CH); 4.29–4.46 (2H, br, NH$_2$).

b) 5-[5-(3-Amino-1,2,4-oxadiazol)-yl]quinuclidine-3-ol. Hydrogen Oxalate

The foregoing quinuclidine (100 mg, 0.48 mmol) in ethanol (5 ml) was treated with sodium borohydride (25 mg, 0.66 mmol) at 25° for 40 min. Excess borohydride was destroyed by dropwise addition of 2M hydrochloric acid, then the solution basified with 2M potassium carbonate and evaporated to dryness. The The residue was extracted twice with boiling ethanol and the extracts filtered and evaporated. Chromatography of the material obtained on alumina in 5% methanol in dichloromethane yielded the desired alcohol as a mixture of all four diastereoisomers (65 mg), which was characterised as the hydrogen oxalate salt. m.p. 48°–55° [Found: m/e (Cl⁻); $(M-H)^-=209.1034$. $C_9H_{13}N_4O_2$ requires $(M-H)^-=209.1039$); $\delta(D_2O)$ ); 1.81–2.00 (2H, m, 8-CH$_2$); 2.65–2.74 (1H, m, 4-CH); 3.14–3.41 (2H, m, 7-CH$_2$); 3.65–3.84 (4H, m, 2-CH$_2$, 6-CH$_2$); 4.01–4.19 (1H, m, 5-CH); 5.42–5.51 (1H, m, 3-CH).

EXAMPLE 38

Tablet Preparation

Tablets containing 1.0, 2.0, 25.0, 26.0, 50.0 and 100.0 mg., respectively, of the following compounds are prepared as illustrated below:

3-[5-(3-amino-1,2,4-oxadiazol)-yl]quinuclidine:

5-[5-(3-amino-1,2,4-oxadiazol)-yl]quinuclidin-3-ol;

1-methyl-3-[5-(3-amino-1,2,4-oxadiazol-yl]pyrrolidine;

3-[5-(3-amino-1,2,4-oxadiazol)-yl]-1-azabicyclo [2,2,1] heptane.

TABLE FOR DOSES CONTAINING FROM 1–25 MG OF THE ACTIVE COMPOUND

| Active Compound | Amount-mg. | | |
|---|---|---|---|
| | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

TABLE FOR DOSES CONTAINING FROM 26–100 MG OF THE ACTIVE COMPOUND

| Active Compound | Amount-mg. | | |
|---|---|---|---|
| | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg, and 100.0 mg of active ingredient per tablet.

We claim:

1. A compound of the formula (I):

or a salt thereof; wherein one of X, Y or Z is an oxygen atom and the other two are nitrogen atoms, and the dotted circle represents aromaticity (two double bonds) thus forming a 1,3,4-oxadiazole or 1,2,4-oxadiazole nucleus; $R^1$ represents a non-aromatic azacyclic or azabicyclic ring system; and $R^2$ represents a substituent of low lipophilicity having a Rekker f value of not greater than 1.5.

2. A compound according to claim 1 wherein the azacyclic or azabicyclic ring system is a non-aromatic ring system containing one nitrogen atom as the sole hereto atom having from 4 to 10 ring atoms and selected from the group consisting of:

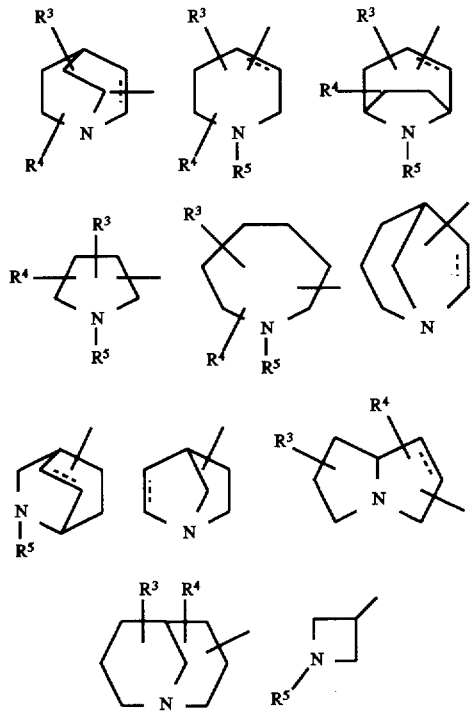

wherein the broken line represents an optional chemical bond;

the substituents $R^3$ and $R^4$ independently represent hydrogen, $C_{1-4}$alkyl, halo, $C_{1-4}$alkoxy, hydroxy or carboxy; or $R^3$ and $R^4$ together represent carbonyl;

the group R⁵ represents hydrogen or $C_{1-4}$alkyl; and the nitrogen atom in the azacyclic or azabicyclic ring system carries a lone pair of electrons.

3. A compound according to claim 2 wherein R² is hydrogen, halo, —CF₃, —OR⁷, —N(R⁷)₂, —NHOR⁷, —NHNH₂, —CN, COR⁸, $C_{2-5}$alkenyl, $C_{2-5}$alkenyl, $C_{1-2}$alkyl, or $C_{1-2}$alkyl substituted with —OR⁷, —N(R⁷)₂, —SR⁷, —CO₂R⁷, —CON(R⁷)₂ or halo; wherein R⁷ is hydrogen or $C_{1-2}$alkyl, and R⁸ represents —OR⁷, NH₂, or NHR⁷.

4. A compound according to claim 2 wherein R¹ is a 5–8 membered nitrogen-containing heterocyclic group selected from:

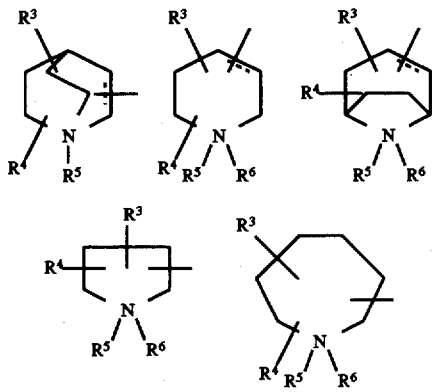

wherein R³ and R⁴ are independently hydrogen, $C_{1-4}$alkyl, halo, $C_{1-4}$alkoxy or hydroxy; R⁵ is hydrogen or $C_{1-4}$alkyl; and R⁶ is a lone pair of electrons; and the broken line represents an optional chemical bond.

5. A compound according to claim 4 wherein R² is hydrogen, halo, —CF₃, —OR⁷, —N(R⁷)₂, $C_{2-5}$alkenyl $C_{2-5}$alkynyl, or $C_{1-2}$alkyl, either unsubstituted or substituted with —OR⁷, —N(R⁷)₂, —SR⁷, —COOR⁷, —CON(R⁷)₂ or halo, wherein R is hydrogen or $C_{1-4}$alkyl.

6. A compound according to claim 5 wherein R¹ is an optionally-substituted quinuclidine ring.

7. A compound according to claim 11 wherein R¹ is a 1-azabicyclo[2.2.1]heptane ring.

8. A compound as claimed in claim 1 which is:

3-[5-(3-amino-1,2,4-oxadiazol)-yl]quinuclidine;

5-[5-(3-amino-1,2,4-oxadiazol)-yl]quinuclidin-3-ol;

1-methyl-3-[5-(3-amino-1,2,4-oxadiazol)-yl]pyrrolidine;

3-[5-(3-amino-1,2,4-oxadiazol)-yl]-1-azabicyclo[2,2,1]heptane;

1-Methyl-3-[5-(3-methyl-1,2,4-oxadiazol)-yl]pyrrolidine;

1-Methyl-3[5-(3-ethyl-1,2,4-oxadiazol)-yl]pyrrolidine;

1,3-Dimethyl-3[5-(3-methyl-1,2,4-oxadiazol)-yl]pyrrolidine;

3-Hydroxy-3-[5-(3-methyl-1,2,4-oxadiazol)-yl]quinuclidine;

2-[5-(3-Methyl-1,2,4-oxadiazol)-yl]-quinuclidine;

1-Methyl-3-[5-(3-methyl-1,2,4-oxadiazol)-yl]1,2,5,6-tetrahydropyridine;

1-Methyl-3-[5-(3-ethyl-1,2,4-oxadiazole)-yl]1,2,5,6-tetrahydropyridine;

1-Methyl-3-[5-(3-methyl-1,2,4-oxadiazol)-yl]piperidine;

1-Methyl-4-[5-(3-methyl-1,2,4-oxadiazol)-yl]piperidine;

3-[3-(5-Methyl-1,2,4-oxadiazol)-yl]quinuclidine;

3-[5-(3-Methyl-1,2,4-oxadiazol)-yl]quinuclidine;

3-[5-(3-Methyl-1,2,4-oxadiazol)-yl]-2,3-dehydroquinucline;

2-Methyl-3-[5-(3-methyl-1,2,4-oxadiazol)-yl]quinuclidine;

2-[5-(3-Methyl-1,2,4-oxadiazol)-yl]-2,3-dehydrotropane;

3-[2-(5-Methyl-1,3,4-oxadiazol)-yl]quinuclidine; and

3-[5-(3-Amino-1,2,4-oxadiazol)-yl]quinuclidine; and salts thereof;

endo-2-[5-(3-Amino-1,2,4-oxadiazol)-yl]pyrrolizidine;

exo-2-[5-(3-Amino-1,2,4-oxadiazol)-yl]pyrrolizidine;

endo and exo-1-[5-(3-Amino-1,2,4-oxadiazol)-yl]pyrrolizidines;

endo and exo-6-[5-(3-Amino-1,2,4-oxadiazol)-yl]-1-azabicyclo[3.2.1octane;

3-[5-(3-Amino-1,2,4-oxadiazol)-yl]pyrrolidine;

endo-6[5-(3-Methyl-1,2,4-oxadiazol)yl]-2-azabicyclo[2.2.2]octane;

exo-6[5-(3-Methyl-1,2,4-oxadiazol)yl]-2-azabicyclo[2.2.2]octane; and

3-[5-(3-Ethoxycarbonyl-1,2,4-oxadiazol)-yl]quinuclidine; and salts thereof;

1-Methyl-3-[5-(3-amino-1,2,4-oxadiazol)-yl]pyrrolidine;

3-[5-(3-Amino-1,2,4-oxadiazol)-yl]-1-azabicyclo[2.2.1]-heptane;

1-Methyl-3[5-(3-amino-1,2,4-oxadiazol)-yl]-1,2,5,6-tetrahydropyridine;

1-Methyl-3[5-(3-amino-1,2,4-oxadiazol)-yl]piperidine;

6-[5-(3-Methyl-1,2,4-oxadiazol)-yl]-1-azabicyclo[3.2.1]-octane;

2-[5-(3-Amino-1,2,4-oxadiazol)-yl]quinuclidine;

3-Hydroxy-3-[5-(3-amino-1,2,4-oxadiazol)-yl]quinuclidine;

2-[5-(3-Methyl-1,2,4-oxadiazol)-yl]-7-azabicyclo[3.2.1]oct-2-ene;

3-[5-(3-chloro-1,2,4-oxadiazol)-yl]quinuclidine;

5-[5-(3-Methyl-1,2,4-oxadiazol)-yl]quinuclidine-3-one;

5-[5-(3-Methyl-1,2,4-oxadiazol)-yl]quinuclidine-3-ol;

5-Methyl-3-[5-(3-methyl-1,2,4-oxadiazol)-yl]quinuclidine;

Methyl 5-[5-(3-Methyl-1,2,4-oxadiazol)-yl]quinuclidine-3-carboxylate;

5-[5-(3-Methyl-1,2,4-oxadiazol)-yl]quinuclidine-3-carboxylic acid;

Methyl 5-[5-(3-Methyl-1,2,4-oxadiazol)yl]quinuclidine-2-carboxylate;

5-[5-(3-Methyl-1,2,4-oxadiazol)-yl]quinuclidine-2-carboxylic acid;

5-[5-(3-Amino-1,2,4-oxadiazol)-yl]-quinuclidine-3-one; and

5-[5-(3-Amino-1,2,4-oxadiazol)-yl]quinuclidine-3-ol; and salts thereof.

9. A pharmaceutical composition which comprises a pharmaceutically acceptable carrier and an effective amount of a compound as claimed in any one of preceeding claims 1–7.

10. A pharmaceutical composition as claimed in claim 9 which further comprises a peripheral cholinergic antagonist.

11. A method of treating neurological or mental disorders which comprises the administration to a patient in need thereof of an effective amount of a compound according to claim 1.

12. A 1,2,4-oxadiazole having the formula (II):

 (II)

or a pharmaceutically acceptable salt thereof; wherein $R^1$ represents a non-aromatic azacyclic or azabicyclic ring system; and $R^2$ represents a low-lipophilic substituent with a Rekker E value $\leq 1.5$.

13. A compound according to claim 12 wherein the azabicyclic ring system is a quinuclidine optionally substituted with methyl or hydroxy.

14. A compound according to claim 12 wherein the azabicyclic ring system is a 1-azabicyclo[2,2,1]heptane ring optionally substituted with methyl or hydroxy.

15. A compound according to claim 12 wherein $R^1$ is a pyrrolidine, optionally substituted with methyl or hydroxy.

16. A compound according to claim 12 wherein the low lipophilic substituent is hydrogen, methyl, amino, methoxycarbonyl or ethoxycarbonyl.

17. A compound according to claim 12 wherein $R^2$ represents amino.

18. A compound according to claim 12 which is:
3-[5-(3-amino-1,2,4-oxadiazol)-yl]quinuclidine;
5-[5-(3-amino-1,2,4-oxadiazol)-yl]quinuclidin-3-ol;
1-methyl-3-[5-(3-amino-1,2,4-oxadiazol) -yl ]pyrrolidine;
3 -[5-(3-amino-1,2,4-oxadiazol)-yl ]-1-azabicyclo [2,2,1 ]heptane.

19. A pharmaceutical composition for treating neurological or mental disorders whose clinical manifestations are due to involvement of cholinergic neurones which comprises a pharmaceutically acceptable carrier and an effective amount of a compound according to claim 12.

20. A pharmaceutical composition according to claim 19 which further comprises a peripheral cholinergic antagonist.

21. A method of treating neurological or mental disorders whose clinical manifestations are due to involvement of cholinergic neurones which comprises the administration to a patient in need thereof, of an effective amount of a compound according to claim 12.

22. A compound of the formula:

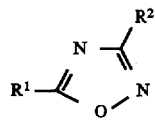

or a pharmaceutically acceptable salt thereof: wherein $R^1$ represents a non-aromatic azabicyclic ring system; and $R^2$ represents a $C_{1-2}$alkyl group.

23. A pharmaceutical composition for treating neurological or mental disorders whose chemical manifestations are due to involvement of cholinergic neurones which comprises a pharmaceutically acceptable carrier and an effective amount of a compound according to claims 22.

24. A method of treating neurological or mental disorders whose clinical manifestations are due to involvement of cholinergic neurones which comprises the administration to a patient in need thereof, of an effective amount of a compound according to claim 22.

* * * * *